US010442840B2

United States Patent
Mueller et al.

(10) Patent No.: US 10,442,840 B2
(45) Date of Patent: Oct. 15, 2019

(54) ARTIFICIAL FORISOME BODY WITH SEO-F FUSION PROTEINS, PLANT OR YEAST CELLS COMPRISING VECTORS WHICH CODE FOR THESE PROTEINS, AS WELL AS VECTORS WHICH CODE FOR SEO-F FUSION PROTEINS

(71) Applicant: Fraunhofer-Gesellschaft zur Foerderung der angewandten Forschung e.V., Munich (DE)

(72) Inventors: Boje Mueller, Muenster (DE); Dirk Pruefer, Muenster (DE); Rainer Fischer, Aachen (DE)

(73) Assignee: Fraunhofer-Gesellschaft zur Foerderung der Angewandten Forchung e.V., Munich (DE)

( * ) Notice: Subject to any disclaimer, the term of this patent is extended or adjusted under 35 U.S.C. 154(b) by 52 days.

(21) Appl. No.: 14/399,472

(22) PCT Filed: May 2, 2013

(86) PCT No.: PCT/EP2013/059190
§ 371 (c)(1),
(2) Date: Nov. 6, 2014

(87) PCT Pub. No.: WO2013/167471
PCT Pub. Date: Nov. 14, 2013

(65) Prior Publication Data
US 2015/0218232 A1  Aug. 6, 2015

(30) Foreign Application Priority Data
May 9, 2012 (EP) .................................. 12167377

(51) Int. Cl.
*C12N 9/04* (2006.01)
*C12N 9/12* (2006.01)
*C12N 9/92* (2006.01)
*C07K 14/415* (2006.01)
*C07K 14/445* (2006.01)

(52) U.S. Cl.
CPC .......... *C07K 14/415* (2013.01); *C07K 14/445* (2013.01); *C12N 9/0006* (2013.01); *C12N 9/1205* (2013.01); *C12N 9/92* (2013.01); *C07K 2319/00* (2013.01); *C12Y 101/01049* (2013.01); *C12Y 207/01001* (2013.01); *C12Y 503/01009* (2013.01)

(58) Field of Classification Search
CPC .............. C07K 14/415; C07K 14/445; C07K 2319/00; C12N 9/0006; C12N 9/1205; C12N 9/92; C12Y 101/01049; C12Y 207/01001; C12Y 503/01009
See application file for complete search history.

(56) References Cited

FOREIGN PATENT DOCUMENTS

WO    03/106501 A1    12/2003

OTHER PUBLICATIONS

Visser et al., Scientific Reports 6:30839; doi:10.1038/srep30839, published on-line Aug. 9, 2016.*
Sadowski et al., Current Opinion in Structural Biology 19:357-362, 2009.*
Starovasnik et al., PNAS 94:10080-10085, 1997.*
Beneteau et al., Plant Physiology 153:1345-1361, 2010.*
Harper et al., Current Protocols in Protein Science 6.6.1-6.6.26, May 2008.*
Muller et al., Annals of Botany 113:1121-1137, 2014.*
G. Noll et al.: "Spatial and temporal regulation of the forisome gene for1 in the phloem during plant development", Plant Mol Biol. vol. 65, 2007, p. 285-294.
A. Shen et al.: "Forisome based biomimetic smart materials", Smart Struct. Syst. vol. 2, 2006, p. 225-235.
K. Uhlig et al.: "A Biohybrid Microfluidic Valve Based on Forisome Protein Complexes", J. Microelectromech. Sys. vol. 17, 2008, p. 1322-1328.
B. Muller et al.: "Recombinant artificial forisomes provide ample quantities of smart biomaterials for use in technical devices", Applied Microbiology and Biotechnology, Springer, Berlin, DE, vol. 88, No. 3, Jul. 28, 2010, p. 689-698.
G. Noll et al.: "Characteristics of artificial forisomes from plants and yeast", Bioengineered Bugs, vol. 2, No. 2, Mar. 1, 2011, p. 1-4.
H. Pelissier et al.: "GFP Tagging of Sieve Element Occlusion (SEO) Proteins Results in Green Fluorescent Forisomes", Plant and Cell Physiology, vol. 49, No. 11, Sep. 10, 2008, p. 1699-1710.
B. Ruping et al.: "Molecular and phylogenetic characterization of the sieve element occlusion gene family in Fabaceae and non-Fabaceae plants", BMC Plant Biology, Biomed Central, London, GB, vol. 10, No. 1, Oct. 8, 2010, p. 219.
A. Shen et al.: "Forisome as biomimetic smart materials", Proceedings of SPIE, vol. 5765, Mar. 7, 2005, p. 97-107.
S. Groscurth et al.: "Artificial Forisomes Are Ideal Models of Forisome Assembly and Activity That Allow the Development of Technical Devices", Biomacromolecules, vol. 13, No. 10, Oct. 8, 2012, p. 3076-3086.
R. Campbell et al.: "A Monomeric Red Fluorescent Protein", PNAS 99(12), 2002, p. 7877-7882.
Noll et al., "Native and Artificial Forisomes: Functions and Applications," Applied Microbiol Biotechnol (2011) 89: 1675-1682.
Notice of Decision for Rejection, Japanese Patent Application No. 2015-510750, dated Nov. 7, 2017.

* cited by examiner

*Primary Examiner* — Delia M Ramirez
(74) *Attorney, Agent, or Firm* — Duane Morris LLP

(57) ABSTRACT

The invention relates to artificial forisome bodies including a fusion protein of at least one SEO-F protein or an at least 50-amino acid portion thereof, and at least one additional protein or peptide, with the exception of GFP and the Venus protein, wherein in an embodiment the forisome body further includes an unfused SEO-F protein or a form of the protein having C-terminal deletions of up to 45 amino acids and/or N-terminal deletions of up to 13 amino acids, wherein the unfused SEO-F protein is selected from proteins having the property of being capable of forming homomeric forisome bodies in the absence of additional SEO-F proteins.

1 Claim, 28 Drawing Sheets

Specification includes a Sequence Listing.

```
<210> SEQ ID:NO 1
<211> 647
<212> PRT
<213> Medicago truncatula
<220>
<221> SOURCE
<222> 1..647
<223> /mol_type="protein"
      /note="MtSEO-F1"
      /organism="Medicago truncatula"
<400> 1
```

| | | | | | | | | | | | | | | |
|---|---|---|---|---|---|---|---|---|---|---|---|---|---|---|
|Met|Ser|Leu|Ser|Asn|Gly|Thr|Lys|Leu|Pro|Asn|Pro|Phe|Asp|Leu|Asp|
|1| | | |5| | | | |10| | | | |15|
|Glu|Ser|Gln|Ile|Leu|Asp|Lys|Val|Tyr|Leu|Thr|His|Leu|His|Asp|Asp|
| | | |20| | | | |25| | | | |30| |
|Asp|Lys|Cys|Asp|Lys|Asp|Val|Leu|Phe|His|Ile|Leu|Ser|Asn|Val|Ile|
| | |35| | | | |40| | | | |45| | |
|Leu|Arg|Thr|Arg|Leu|Ala|Glu|Ser|Arg|Ala|Glu|Phe|Glu|Pro|Glu|Phe|
| |50| | | | |55| | | | |60| | | |
|Arg|Thr|Leu|Lys|Leu|Ile|Ser|Cys|Gln|Met|Ile|Thr|Thr|Pro|Arg|Gly|
|65| | | | |70| | | | |75| | | | |80|
|Glu|Arg|Tyr|Val|His|Gln|Thr|Thr|Met|Trp|Ile|Leu|Gln|Gln|Leu|Lys|
| | | | |85| | | | |90| | | | |95| |
|Thr|Tyr|Ser|Trp|Asp|Ala|Lys|Ala|Leu|Ile|Ala|Leu|Ala|Ala|Phe|Thr|
| | | |100| | | | |105| | | | |110| | |
|Leu|Glu|Tyr|Gly|Asn|Leu|Leu|Tyr|Leu|Thr|Glu|Thr|Ser|Thr|Ser|Ser|
| | | |115| | | | |120| | | | |125| | |
|Asp|Gln|Leu|Val|Asn|Ser|Leu|Lys|Ile|Leu|Asn|Gln|Ile|Gln|Asn|Arg|
| | |130| | | | |135| | | | |140| | | |
|Lys|Val|Thr|Val|Pro|Ala|Thr|Asp|Leu|Val|Glu|Leu|Ile|Met|Asp|Val|
|145| | | | |150| | | | |155| | | | |160|
|Leu|Leu|His|Ile|His|Glu|Trp|Ala|Thr|Arg|Ser|Gly|Val|Gly|Tyr|Asn|
| | | | |165| | | | |170| | | | |175| |
|Thr|Leu|Asp|Val|Pro|Ser|Leu|Ser|Asp|Ala|Leu|Gln|Asp|Ile|Pro|Val|
| | | |180| | | | |185| | | | |190| | |
|Ala|Val|Tyr|Trp|Ile|Ile|Ala|Ser|Thr|Val|Ala|Ala|Thr|Gly|Asn|Ile|
| | |195| | | | |200| | | | |205| | | |
|Ile|Gly|Val|Ser|Asp|Tyr|Thr|Leu|Ser|Asp|Phe|Lys|Glu|Lys|Leu|Asn|
| | |210| | | | |215| | | | |220| | | |
|Phe|Val|Asp|Ser|Lys|Leu|Lys|Glu|His|Leu|Lys|Leu|Ser|Lys|Trp|Gln|
|225| | | | |230| | | | |235| | | | |240|
|Ile|Asp|Ser|Val|Glu|Glu|Tyr|Leu|Lys|Arg|Lys|Lys|Ala|Ile|Ser|Asn|
| | | | |245| | | | |250| | | | |255| |
|Pro|Lys|Asp|Ile|Ile|Asp|Phe|Leu|Lys|Leu|Leu|Ile|Gln|Arg|Asn|Gly|

Figure 1

```
                        260                     265                     270
        Asp Asn Leu Leu Ile Tyr Asp Gly Thr Thr Lys Asn Lys Thr Asp Ile
                    275                     280                     285
        Glu Val Phe Lys Asp Lys Tyr Val Leu Leu Phe Ile Ser Ser Leu Asn
                290                     295                     300
        Lys Val Asp Asp Glu Ile Leu Leu Leu Asn Ser Ile His Asp Arg Leu
        305                     310                     315                     320
        Gln Asp Asn Pro Gln Val Ile Lys Gly Tyr Lys Lys Glu Asp Phe Lys
                        325                     330                     335
        Ile Leu Trp Ile Pro Ile Trp Asp Val Asp Asp Gln Lys Ile Lys Phe
                    340                     345                     350
        Asp Ser Leu Lys Asn Lys Ile Arg Phe Tyr Ala Val Asp Tyr Phe Ser
                    355                     360                     365
        Glu Leu Pro Gly Ile Arg Leu Ile Arg Glu His Leu Asn Tyr Ser Asp
                370                     375                     380
        Lys Pro Ile Val Pro Val Leu Ser Pro Leu Gly Glu Lys Met Asn Asp
        385                     390                     395                     400
        Asp Ala Met Asp Leu Ile Phe Gln Trp Gly Ile Asp Ala Leu Pro Phe
                        405                     410                     415
        Arg Lys Gln Asp Gly Tyr Asp Leu Thr Gln Lys Trp Lys Trp Phe Trp
                    420                     425                     430
        Asp Val Thr Lys Arg Val Asn Leu Gly Ile Gln Val Lys Gly Asp Arg
                    435                     440                     445
        Tyr Ile Phe Ile Tyr Gly Gly Ser Asp Lys Lys Trp Ile Gln Asp Phe
                450                     455                     460
        Thr Leu Ala Leu Glu Lys Thr Lys Arg His Glu Thr Ile Leu Arg Ala
        465                     470                     475                     480
        Asp Ala Ile Ile Glu His Tyr His Leu Gly Lys Asp Asp Pro Lys Ile
                        485                     490                     495
        Val Pro Arg Phe Trp Ile Glu Ile Glu Ser Lys Arg Leu Lys Lys His
                    500                     505                     510
        Gln Asp Gly Ile Asp Cys Glu Ile Gln Asp Ile Val Lys Ser Leu Leu
                    515                     520                     525
        Cys Leu Lys Gln Asp Pro Gln Gly Trp Val Ile Leu Thr Lys Gly Tyr
                530                     535                     540
        Asn Val Lys Leu Leu Gly His Gly Glu Pro Met Tyr Gln Thr Leu Ala
        545                     550                     555                     560
        Asp Phe Asp Ile Trp Lys Asp Arg Val Leu Gln Lys Glu Gly Phe Asp
                        565                     570                     575
        Ile Ala Phe Lys Glu Tyr Tyr Asp Thr Lys Val Lys Asp Thr Tyr Val
                    580                     585                     590
        Lys Gln Pro Cys Glu Ile Ile Asn Val Asp Asn Asn Ile Asn Gly Asn
                    595                     600                     605
        Val Ile Ala Thr Ile Ser Cys Pro Asn Pro Thr Cys Gly Arg Val Met
```

Figure 1 (continued)

```
        610                 615                 620
Glu Val Ser Ser Val Asn Tyr Lys Cys Cys His Arg Asp Asp Ala Ala
625                 630                 635                 640
Ala Pro Gln Asn Gly Lys Ile
                    645
```

Figure 1 (continued)

```
<210> 2
<211> 675
<212> PRT
<213> Medicago truncatula
<220>
<221> SOURCE
<222> 1..675
<223> /mol_type="protein"
      /note="MtSEO-F2"
      /organism="Medicago truncatula"
<400> 2
```

| | | | | | | | | | | | | | | |
|---|---|---|---|---|---|---|---|---|---|---|---|---|---|---|
| Met | Ser | Thr | Ala | Leu | Ser | Tyr | Asn | Val | Pro | Ile | Ser | Gly | Thr | Thr |
| 1 | | | | 5 | | | | | 10 | | | | | 15 |
| Gln | Lys | Asn | Asp | Thr | Ser | Gln | Gln | Gln | Lys | Ser | Gln | Leu | Pro | Asn | Pro |
| | | | 20 | | | | | 25 | | | | | 30 | | |
| Phe | Lys | Leu | Glu | Asp | Ile | Glu | Ile | Leu | Asn | Lys | Val | Tyr | Leu | Thr | His |
| | | 35 | | | | | 40 | | | | | 45 | | | |
| Val | Asn | Asp | Asn | Met | Lys | Tyr | Asp | Arg | Asp | Thr | Leu | Phe | Asn | Leu | Val |
| | 50 | | | | | 55 | | | | | 60 | | | | |
| Ser | Asn | Ile | Ile | Ser | Ala | Ser | Thr | Gln | Thr | Ser | Gly | Thr | Asn | Ser | Gly |
| 65 | | | | | 70 | | | | | 75 | | | | | 80 |
| Leu | Asn | Thr | Gln | Ile | Ser | Phe | Lys | Pro | Asp | Phe | Ser | Val | Leu | Lys | Arg |
| | | | | 85 | | | | | 90 | | | | | 95 | |
| Ile | Ser | Cys | Gln | Met | Ile | Thr | Thr | Arg | Gly | Thr | Ala | Glu | Cys | Ala | His |
| | | | 100 | | | | | 105 | | | | | 110 | | |
| Gln | Thr | Thr | Met | Trp | Val | Leu | His | His | Leu | Arg | Gly | Phe | Ser | Trp | Glu |
| | | 115 | | | | | 120 | | | | | 125 | | | |
| Ala | Lys | Ala | Leu | Ile | Thr | Leu | Ala | Ala | Phe | Ser | Leu | Glu | Tyr | Gly | Ala |
| | 130 | | | | | 135 | | | | | 140 | | | | |
| Ile | Met | His | Leu | His | Arg | Ile | Gln | Ser | Ser | Asp | Thr | Leu | Gly | Asn | Ser |
| 145 | | | | | 150 | | | | | 155 | | | | | 160 |
| Leu | Lys | Gln | Leu | Ser | Gln | Val | Gln | Phe | Arg | Lys | Val | Pro | Ala | Asp | Ile |
| | | | | 165 | | | | | 170 | | | | | 175 | |
| Thr | Glu | Leu | Val | Thr | Phe | Leu | Leu | Gln | Val | Leu | Gln | Asp | Ile | Lys | Thr |
| | | | 180 | | | | | 185 | | | | | 190 | | |
| Trp | Ala | Ala | Trp | Ser | Ala | Phe | Gly | Tyr | Asp | Leu | Asp | Asp | Val | Asn | Ser |
| | | 195 | | | | | 200 | | | | | 205 | | | |
| Leu | Pro | Asp | Ala | Met | Gln | Trp | Ile | Pro | Leu | Val | Val | Tyr | Trp | Thr | Val |
| | 210 | | | | | 215 | | | | | 220 | | | | |
| Ala | Thr | Ile | Val | Ala | Cys | Thr | Gly | Asn | Leu | Val | Gly | Ile | Ser | Glu | His |
| 225 | | | | | 230 | | | | | 235 | | | | | 240 |
| Lys | Leu | Ser | Asp | Tyr | Val | Lys | Ser | Leu | Ser | Asp | Val | Val | Lys | Glu | Leu |
| | | | | 245 | | | | | 250 | | | | | 255 | |
| Arg | Arg | His | Leu | Lys | Ser | Cys | Glu | Leu | Glu | Ile | Gly | Lys | Ile | His | Glu |

Figure 2

```
                    260                           265                           270
Asn Glu Asn Leu Leu Lys Asp Ser Asp Asn Ile Lys Asp Val Val Ala
            275                           280                           285
Phe Leu Arg Leu Leu Ile Lys Gly Asn Gly Thr Asp Gln Ile Pro Pro
            290                           295                           300
Ile Phe Ile Gly Asn Asp Gln Val Lys Thr Gly Ile Glu Val Phe Lys
305                           310                           315               320
Lys Lys His Val Leu Leu Phe Val Ser Gly Leu Asp Thr Leu Arg Asp
                    325                           330                   335
Glu Ile Leu Leu Leu Asn Ser Ile Tyr Lys Arg Leu Gln Asp Lys Pro
                    340                           345                   350
Gln Glu Val Leu Lys Gly Ser Phe Lys Lys Glu Asp Phe Lys Ile Leu
            355                           360                   365
Trp Ile Pro Ile Val Asn Lys Trp Asp Glu Asp Arg Lys Lys Glu Phe
            370                           375                   380
Lys Asn Leu Lys Glu Ser Met Lys Trp Tyr Val Leu Glu His Phe Ser
385                           390                           395               400
Glu Leu Pro Gly Arg Gly Ile Ile Lys Lys Lys Leu Asn Tyr Asp Ile
                    405                           410                   415
Gly Tyr Pro Pro Ile Leu Ala Val Ile Asn Pro Gln Gly Asp Ile Ile
                    420                           425                   430
Asn Lys Asp Ala Met Glu Ile Ile Phe Gln Trp Gly Ile Asp Ala Phe
            435                           440                   445
Pro Phe Arg Ile Ser Asp Ala Glu Asp Ile Phe Lys Lys Trp Glu Trp
            450                           455                   460
Phe Trp Lys Leu Met Lys Lys Val Asp Val Asn Ile Glu Lys Met Ser
465                           470                           475               480
Trp Asp Arg Tyr Ile Phe Ile Tyr Gly Gly Asn Asp Pro Lys Trp Ile
                    485                           490                   495
Gln Asp Phe Thr Arg Ala Ile Gly Ser Ile Lys Lys His Gln Thr Ile
            500                           505                   510
Gln Asn Val Asp Val Asn Ile Asp Tyr His Gln Leu Gly Lys Asn Asn
            515                           520                   525
Pro Thr Glu Ile Pro Tyr Phe Trp Met Gly Ile Asp Gly Arg Lys Gln
530                           535                           540
Gln Asn Lys Thr Cys Lys Asp Ser Val Asp Cys Glu Ile Gln Thr Ala
545                           550                           555               560
Val Lys Lys Leu Leu Cys Leu Lys Gln Asp Pro Leu Gly Trp Val Leu
                    565                           570                   575
Leu Ser Arg Gly Arg His Val Thr Val Phe Gly His Gly Glu Pro Met
            580                           585                   590
Tyr Gln Thr Val Ala Asp Phe Asp Lys Trp Lys Asn Asn Val Val Glu
            595                           600                   605
Lys Glu Ser Phe Asp Glu Ala Phe Lys Glu Tyr Tyr Asp Thr Lys Leu
```

Figure 2 (continued)

```
            610                     615                     620
Ser Glu Ile Ser Ser Ser Ala Ser Cys Ala Val Asn Ser Ser Asp Val
625                     630                     635                     640
Leu Ala Thr Ile Thr Cys Pro Asn Pro Phe Cys Gly Arg Val Met Glu
                    645                     650                     655
Val Thr Ser Val Asn Tyr Lys Cys Cys His Arg Asp Asp Pro Asp Ser
                660                     665                     670
Cys Cys Ile
        675
```

Figure 2 (continued)

```
<210> SEQ ID-Nr:3
<211> 701
<212> PRT
<213> Medicago truncatula

<220>
<221> SOURCE
<222> 1..701
<223> /mol_type="protein"
     /note="MtSEO-F3"
     /organism="Medicago truncatula"
<400> 3
Met Ser Ser Ser Met Ala Pro Ser Ser Leu Val Ser Asn Val Ser Ala
1               5                   10                  15
Tyr Ser Gln Gln Ala Arg Thr Ser Asn Pro Leu Ala Trp Ser Asp Asp
                20                  25                  30
Lys Ile Leu Glu Thr Val Tyr Leu Thr His Val His Thr Gly Glu Arg
            35                  40                  45
Tyr Asp Val Glu Ser Leu Phe Asn Leu Thr Ser Asn Ile Leu Lys Arg
        50                  55                  60
Ser Thr Ala Val Ala Asp Ser Val Ala Ser Lys Thr Gly Thr Pro Val
65                  70                  75                  80
Gly Leu Val Glu Asp Arg Leu Pro Leu Ser Gly Tyr Glu Pro Pro Ile
                85                  90                  95
Arg Lys Leu Lys His Ile Ser Ala Gln Met Met Ser Thr Leu Pro Gly
            100                 105                 110
Glu His His Ala His Met Thr Thr Met Ser Ile Leu Asp Gln Leu Lys
        115                 120                 125
Ser His Thr Trp Asp Gly Lys Ala Ile Phe Ala Leu Ala Ala Phe Ser
    130                 135                 140
Leu Glu Tyr Gly Asn Phe Trp His Leu Val Gln Thr Pro Ser Gly Asp
145                 150                 155                 160
Thr Leu Gly Arg Ser Leu Ala Thr Met Asn Arg Val Gln Ser Val Asp
                165                 170                 175
Lys Asn Arg Gln Ala Ile Ala Asp Tyr Asn Ser Leu Val Lys Asn Leu
            180                 185                 190
Leu Phe Ala Val Glu Cys Ile Thr Glu Leu Glu Lys Leu Ser Thr Lys
        195                 200                 205
Gly Tyr Glu His Lys Asp Val Pro Ala Leu Ser Glu Ala Met Gln Glu
    210                 215                 220
Ile Pro Val Ala Val Tyr Trp Ala Ile Ile Thr Ala Ile Ile Cys Ala
225                 230                 235                 240
Asn His Leu Asp Leu Leu Phe Gly Asp Ser Asp Asp Arg Tyr Glu Leu
                245                 250                 255
```

Figure 3

```
Ser Ser Tyr Asp Val Lys Leu Ala Ser Ile Val Ser Lys Leu Lys Ala
            260                 265                 270
His Leu Thr Arg Ser Arg Lys His Ile Gly Glu Leu Glu Asp Tyr Trp
            275                 280                 285
Arg Arg Lys Arg Val Leu Gln Thr Pro Thr Glu Ile Val Glu Val Leu
    290                 295                 300
Lys Val Leu Val Phe His Asn Glu Ile Gln Asp Pro Leu Val Phe Asp
305                 310                 315                 320
Gly Leu Asn Arg Gln Met Val Ser Ile Glu Val Phe Arg Lys Lys His
                325                 330                 335
Val Leu Val Phe Ile Ser Gly Leu Asp Ser Ile Arg Asp Glu Ile Arg
            340                 345                 350
Leu Leu Gln Ser Ile Tyr Val Gly Leu Gln Glu Glu Pro Arg Glu Leu
            355                 360                 365
Lys Gly Tyr Arg Lys Glu Asp Phe Lys Ile Leu Trp Ile Pro Ile Val
        370                 375                 380
Asp Asp Trp Thr Leu Leu His Lys Ala Glu Phe Asp Asn Leu Lys Leu
385                 390                 395                 400
Glu Met Pro Trp Tyr Val Val Glu Tyr Phe Tyr Pro Leu Ala Gly Ile
                405                 410                 415
Arg Leu Ile Arg Glu Asp Leu Ser Tyr Lys Asn Lys Pro Ile Leu Pro
            420                 425                 430
Val Leu Asn Pro Leu Gly Arg Ile Val Asn His Asn Ala Met His Met
            435                 440                 445
Ile Phe Val Trp Gly Ile Asp Ala Phe Pro Phe Arg Pro Thr Asp Asp
        450                 455                 460
Glu Ser Leu Thr Gln Lys Trp Asn Trp Phe Trp Ala Glu Met Lys Lys
465                 470                 475                 480
Val Tyr Pro Arg Leu Gln Asp Leu Ile Lys Gly Asp Thr Phe Ile Phe
                485                 490                 495
Ile Tyr Gly Gly Thr Asp Pro Lys Trp Thr Gln Asp Phe Ala Leu Ala
            500                 505                 510
Ile Glu Lys Ile Lys Arg His Glu Ile Thr Arg Lys Ala Asp Ala Val
        515                 520                 525
Ile Glu His Phe His Phe Gly Lys Glu Asp Lys Arg Ile Val Pro Arg
    530                 535                 540
Phe Trp Ile Gly Ile Glu Ser Leu Phe Ala Asn Met Ile Gln Lys Lys
545                 550                 555                 560
His Lys Asp Pro Thr Ile Asp Glu Ile Lys Ser Leu Leu Cys Leu Lys
                565                 570                 575
Gln Asp Gln Pro Gly Trp Val Leu Leu Ser Lys Gly Pro Asn Val Lys
            580                 585                 590
Leu Leu Gly Arg Gly Asp Gln Met Tyr Ala Thr Ala Val Asp Phe Glu
        595                 600                 605
```

Figure 3 (continued)

```
Ile Trp Lys Glu Lys Val Leu Glu Lys Ala Gly Phe Asp Val Ala Phe
    610                 615                 620
Lys Glu Tyr Tyr Glu Arg Lys Arg Arg Glu Tyr Pro Val Ala Cys Ala
625                 630                 635                 640
Asn Met Gln Leu Ala Asn Tyr Pro Ser Asp Ile Leu Asp Pro Ile Tyr
                645                 650                 655
Cys Pro Asp Ser Asn Cys Gly Arg Ser Met Glu Ile Ala Ser Val Ser
            660                 665                 670
Tyr Lys Cys Cys His Gly His Thr His Glu Asn Ala Glu Val Ala Pro
        675                 680                 685
Ala Glu Ser Gly Gly Phe Val Gln Ile Glu Lys Arg Ser
    690                 695                 700
```

Figure 3 (continued)

```
<210> SEQ ID-NO:4
<211> 671
<212> PRT
<213> Medicago truncatula

<220>
<221> SOURCE
<222> 1..671
<223> /mol_type="protein"
     /note="MtSEO-F4"
     /organism="Medicago truncatula"
<400> 4
```

| | | | | | | | | | | | | | | |
|---|---|---|---|---|---|---|---|---|---|---|---|---|---|---|
| Met | Ser | Leu | Ser | Asn | Leu | Gly | Ser | Ala | Thr | Ala | Thr | Asn | Ser | Ser | Leu |
| 1 | | | | 5 | | | | | 10 | | | | | 15 | |
| Asn | Gln | Lys | Asn | Ala | Thr | Asn | Ser | Leu | Gln | Asn | Lys | Ala | Asn | Phe | Leu |
| | | | 20 | | | | | 25 | | | | | 30 | | |
| Pro | Asn | Pro | Phe | Asp | Leu | His | Asp | Pro | Gln | Ile | Leu | Asp | Arg | Val | Tyr |
| | | 35 | | | | | 40 | | | | | 45 | | | |
| Leu | Thr | His | Val | Thr | Asp | Asp | Glu | Phe | Cys | Asp | Thr | Asn | Ile | Ile | Phe |
| | 50 | | | | | 55 | | | | | 60 | | | | |
| Glu | Leu | Val | Ser | Ser | Val | Val | Leu | Gln | Thr | Ile | Pro | Lys | Ile | Ser | Val |
| 65 | | | | | 70 | | | | | 75 | | | | | 80 |
| Thr | Ser | Phe | Lys | Pro | Glu | Phe | Pro | Thr | Leu | Lys | Leu | Ile | Ser | Cys | Gln |
| | | | | 85 | | | | | 90 | | | | | 95 | |
| Met | Ile | Thr | Thr | Arg | Asn | Asp | Pro | His | Cys | Val | His | Gln | Thr | Thr | Leu |
| | | | 100 | | | | | 105 | | | | | 110 | | |
| Trp | Ile | Leu | Gln | Asn | Leu | Arg | Ser | Tyr | Ser | Trp | Asp | Ala | Lys | Ala | Leu |
| | | 115 | | | | | 120 | | | | | 125 | | | |
| Ile | Thr | Leu | Ala | Ala | Phe | Thr | Leu | Glu | Tyr | Gly | Asn | Tyr | Leu | Gln | Leu |
| | 130 | | | | | 135 | | | | | 140 | | | | |
| Asn | Arg | Val | Thr | Thr | Thr | Asp | Thr | Leu | Gly | Asn | Ser | Leu | Arg | Val | Leu |
| 145 | | | | | 150 | | | | | 155 | | | | | 160 |
| Asn | Gln | Val | Gln | Thr | Arg | Lys | Ile | Ser | Asn | Asp | Val | Thr | Glu | Leu | Val |
| | | | | 165 | | | | | 170 | | | | | 175 | |
| Lys | Tyr | Ile | Val | Asp | Met | Leu | Ile | His | Leu | Asn | Val | Trp | Ala | Thr | Trp |
| | | | 180 | | | | | 185 | | | | | 190 | | |
| Ser | Ala | Asp | Gly | Tyr | Asp | Pro | Val | Asp | Val | Pro | Ala | Leu | Thr | Asp | Ala |
| | | 195 | | | | | 200 | | | | | 205 | | | |
| Leu | Gln | Glu | Ile | Pro | Val | Phe | Val | Tyr | Trp | Thr | Ile | Ala | Ser | Ile | Val |
| | 210 | | | | | 215 | | | | | 220 | | | | |
| Ala | Ser | Thr | Gly | Asn | Leu | Val | Gly | Val | Ser | Asp | Tyr | Lys | Leu | Ser | Ala |
| 225 | | | | | 230 | | | | | 235 | | | | | 240 |
| Tyr | Lys | Glu | Arg | Leu | Ser | Arg | Val | Val | Glu | Glu | Leu | Val | Lys | His | Leu |
| | | | | 245 | | | | | 250 | | | | | 255 | |

Figure 4

```
Ala Thr Cys Glu Arg Gln Ile Arg Asn Val Asp Asp Leu Thr Ser Arg
            260                 265                 270
Thr Asn Asn Tyr Arg Lys Pro Lys Asp Ile Val Asp Cys Leu Lys Ala
        275                 280                 285
Leu Ile His Arg Asn Gly Thr Asp Ile Pro Gln Ile Tyr Gln Gly Asn
        290                 295                 300
Val Gln Val Lys Ser Gly Leu Asp Ile Phe Lys Gln Lys His Val Leu
305                 310                 315                 320
Leu Phe Ile Ser Ser Leu Asp Arg Ile Gln Asp Glu Ile Thr Leu Leu
                325                 330                 335
Asn Ser Ile Tyr Glu Arg Leu Gln Glu Asn Pro Lys Glu Ser Lys Gly
                340                 345                 350
Phe Met Lys Glu Asp Phe Lys Ile Leu Trp Ile Pro Ile Val Lys Lys
            355                 360                 365
Trp Asp Asp Ile Gln Ile Glu Asn Phe Lys Ala Leu Lys Ser Gly Ile
        370                 375                 380
Lys Trp Tyr Val Val Glu Tyr Phe Ser Glu Leu Pro Gly Leu Lys Ile
385                 390                 395                 400
Ile Lys Asp Pro Glu Leu Ile Gly Tyr Ile Asp Asn Pro Ile Ile Pro
                405                 410                 415
Val Phe Asn Pro Lys Gly Ile Ile Thr Asn Glu Asp Ala Met Asp Leu
                420                 425                 430
Ile Phe Gln Trp Gly Ile Asp Ala Phe Pro Phe Arg Lys Ser Asp Gly
            435                 440                 445
Asn Asp Leu Lys Leu Lys Trp Asn Trp Leu Trp Asp Val Ile Lys Lys
        450                 455                 460
Ala Thr Pro Gly Leu Leu Val Lys Val Asp Arg Tyr Ile Phe Ile Tyr
465                 470                 475                 480
Gly Gly Thr Asn Lys Lys Trp Ile Gln Asp Phe Thr Leu Glu Leu Glu
                485                 490                 495
Lys Ile Lys Arg His Glu Thr Ile Lys Arg Ala Asp Val Ile Ile Glu
                500                 505                 510
Asn Tyr Gln Val Gly Lys Asp Pro Asn Arg Val Pro Ser Phe Trp
        515                 520                 525
Met Gly Ile Glu Arg Lys Lys Gln Asn Lys Lys His Gln Glu Thr Val
        530                 535                 540
Asp Cys Lys Ile Gln Glu Ile Val Lys Asp Leu Phe Cys Leu Arg Arg
545                 550                 555                 560
Asp Pro Gln Gly Trp Ile Ile Leu Ser Lys Gly His Ser Ile Lys Leu
                565                 570                 575
Leu Gly His Gly Glu Pro Ala Tyr Gln Thr Leu Val Glu Phe Gln Asn
                580                 585                 590
Trp Lys Asp Lys Val Leu Glu Lys Glu Gly Phe Asp Ile Ala Phe Lys
            595                 600                 605
```

Figure 4 (continued)

```
Glu Tyr Tyr Gln Met Lys Ala Lys Glu Ile Ser Gly Arg Glu Pro Cys
        610                 615                 620
Glu Val Leu Asn Val Asp Thr Tyr Ser Ser Asn Val Ile Gly Thr Ile
625                 630                 635                 640
Ser Cys Pro Asn Pro Met Cys Gly Arg Val Met Glu Val Ser Ser Ile
                645                 650                 655
His Tyr Lys Cys Cys His Arg Asp Glu Pro Asn Asn Leu Gly Val
        660                 665                 670
```

Figure 4 (continued)

```
<210> SEQ ID-NO:5
<211> 651
<212> PRT
<213> Dipteryx panamensis

<220>
<221> SOURCE
<222> 1..651
<223> /mol_type="protein"
     /organism="Dipteryx panamensis"

<400> 5
```

Met Ser Leu Ser Asn Gly Ala Ser Ser Thr Thr Leu Ser Gln Gln Lys
1               5                   10                  15
Thr Gln Leu Pro Asn Pro Phe Asp Leu Thr Asp Ser Gln Ile Leu Asp
            20                  25                  30
Lys Val Tyr Leu Ser His Ala His Asp Asp Glu Glu Cys Asp Arg Asp
        35                  40                  45
Thr Leu Leu Asp Leu Val Ser Ile Ile Ile Leu Lys Ser Gln Arg Pro
    50                  55                  60
Ile Pro Leu Ala Lys Tyr Lys Pro Glu Phe Pro Thr Leu Lys Leu Ile
65                  70                  75                  80
Ser Cys Gln Met Ile Thr Thr Arg Gly Val Val His Cys Ala His Gln
            85                  90                  95
Thr Thr Met Trp Ile Leu Gln His Leu Arg Ser Phe Ser Trp Asp Ala
            100                 105                 110
Lys Ala Leu Ile Thr Val Ala Ala Phe Ser Leu Glu Tyr Gly Asn Phe
        115                 120                 125
Arg His Leu Gln Ile Pro Thr Ser Asp Gln Leu Gly Asn Ala Leu Lys
    130                 135                 140
Gln Leu Asn Gln Val Asn Asn Gly Lys Leu Ser Asp Asp Ile Thr Glu
145                 150                 155                 160
Leu Ala Thr Val Thr Val Arg Val Leu Gln His Leu Lys Glu Trp Ala
            165                 170                 175
Ala Trp Ser Ala Ala Gly Tyr Asp Thr Glu Asp Val Pro Ala Leu Ser
            180                 185                 190
Asp Ala Leu Gln Val Ile Pro Phe Val Val Tyr Trp Thr Ile Ala Ser
        195                 200                 205
Ile Val Ala Ser Thr Gly Asn Leu Ile Gly Val Ser Asp Tyr Lys Leu
    210                 215                 220
Ser Asp Phe Lys Asp Lys Leu Asp Arg Val Val Lys Thr Leu Asn Asp
225                 230                 235                 240
His Leu Asp Glu Cys Lys Lys Gln Ile Asp Val Ile Asp Asn Tyr Asn
            245                 250                 255
Trp Arg Arg Lys Ala Phe Glu Asn Pro Lys Asp Ile Val Asp Leu Leu
            260                 265                 270

Figure 9

```
Lys Leu Leu Ile His Ser Lys Gly Ser Pro Ile Pro Gln Ile Tyr Asp
            275                 280                 285
Gly Arg Thr Thr Thr Lys Thr Asp Ile Glu Val Phe Lys Gln Lys Tyr
        290                 295                 300
Val Leu Leu Phe Ile Ser Ser Leu Asp Ser Ile Asp Asp Glu Ile Arg
305                 310                 315                 320
Leu Leu Asn Ser Ile Tyr Asp Arg Leu Lys Glu Asp Pro Lys Glu Val
                325                 330                 335
Lys Gly Phe Asn Lys Glu Asp Phe Lys Ile Leu Trp Ile Pro Ile Val
            340                 345                 350
Asp Ser Trp Asp Lys Asp Ser Val Glu Lys Tyr Lys Thr Leu Lys Thr
        355                 360                 365
Lys Ile Lys Trp Tyr Ala Val Glu Phe Leu Ser Leu Val Pro Gly Ile
    370                 375                 380
Arg Leu Val Arg Glu Val Leu Lys Phe Glu Thr Lys Pro Ile Ile Pro
385                 390                 395                 400
Val Ile Ser Pro Gln Gly Lys Arg Ile Asn Asp Asn Ala Met Asp Ile
                405                 410                 415
Ile Phe Glu Trp Gly Val Asp Ala Phe Pro Phe Arg Lys Glu Asp Gly
            420                 425                 430
Asp Gln Leu Thr Gln Lys Trp Lys Trp Phe Trp Asp Val Ile Lys Lys
        435                 440                 445
Val Asn Pro Ala Ile Gln Val Glu Pro Glu Ser Tyr Ile Phe Ile Tyr
    450                 455                 460
Gly Gly Thr Asp Asn Lys Trp Ile Gln Asp Phe Thr Leu Ala Val Asp
465                 470                 475                 480
Lys Val Lys Arg His Asp Thr Ile Lys Arg Ala Asp Ala Ile Ile Glu
                485                 490                 495
His His Gln Leu Ala Lys Asp Ser Ile Val Pro Arg Phe Trp Ile
            500                 505                 510
Gly Ile Glu Ser Lys Thr His Lys Lys His Gln Glu Ala Val Asp Cys
        515                 520                 525
Gln Ile Gln Thr Ile Val Lys Ser Leu Leu Cys Leu Lys Arg Asp Pro
    530                 535                 540
Gln Gly Trp Ala Ile Leu Ser Lys Gly Asn Asn Val Lys Ile Leu Gly
545                 550                 555                 560
His Gly Glu Pro Met Leu Gln Thr Leu Thr Gln Phe Glu Ser Trp Lys
                565                 570                 575
Asp Lys Val Leu Glu Lys Glu Gly Phe Asp Ile Ala Leu Lys Glu Phe
            580                 585                 590
Tyr Asp Gly Lys Val Glu Ser Leu Ser Tyr Arg Gln Pro Cys Glu Tyr
        595                 600                 605
Leu Asn Ile Asp Ser Gln Ser Ser Ser Val Ile Ala Thr Ile Thr Cys
    610                 615                 620
Pro Asn Pro Thr Cys Gly Arg Val Met Glu Val Thr Ser Val Asn Tyr
625                 630                 635                 640
Arg Cys Cys His Arg Asp Gly Gln Lys Ile Cys
```

```
<210> SEQ ID-NO:6
<211> 668
<212> PRT
<213> Lotus japonicus

<220>
<221> SOURCE
<222> 1..668
<223> /mol_type="protein"
     /organism="Lotus japonicus"

<400> 6
```

| | | | | | | | | | | | | | | |
|---|---|---|---|---|---|---|---|---|---|---|---|---|---|---|
| Met | Ser | His | Val | Pro | Lys | Ala | Ala | Ser | Asn | Gly | Ala | Leu | Ile | Gln | His |
| 1 | | | | 5 | | | | | 10 | | | | | 15 | |
| Ser | Gly | Thr | Ser | Pro | Asn | Gln | Lys | Ala | Tyr | Leu | Pro | Ser | Pro | Phe | Glu |
| | | | | 20 | | | | | 25 | | | | | 30 | |
| Leu | Lys | Asp | Pro | Gln | Ile | Leu | Asp | Arg | Val | Tyr | Leu | Thr | His | Val | Asn |
| | | | 35 | | | | | 40 | | | | | 45 | | |
| Asp | Asp | Glu | Ile | Cys | Asp | Thr | Lys | Ile | Leu | Phe | Asp | Leu | Val | Ser | Thr |
| | | | 50 | | | | | 55 | | | | | 60 | | |
| Val | Val | Leu | Gln | Ser | Val | Ser | Gln | Ile | Pro | Ala | Thr | Ser | Phe | Lys | Pro |
| 65 | | | | | 70 | | | | | 75 | | | | | 80 |
| Glu | Phe | Ser | Thr | Leu | Lys | Leu | Ile | Ser | Cys | Gln | Met | Ile | Thr | Thr | Arg |
| | | | | 85 | | | | | 90 | | | | | 95 | |
| Asn | Ala | Asp | His | Cys | Val | His | Gln | Thr | Thr | Met | Trp | Ile | Leu | Gln | Asn |
| | | | | 100 | | | | | 105 | | | | | 110 | |
| Leu | Arg | Ser | Tyr | Ser | Trp | Asp | Ala | Lys | Ala | Ile | Ile | Thr | Leu | Ala | Ala |
| | | | 115 | | | | | 120 | | | | | 125 | | |
| Phe | Thr | Leu | Glu | Tyr | Gly | Asn | Tyr | Leu | His | Leu | Ser | Arg | Ala | Ala | Val |
| | | 130 | | | | | 135 | | | | | 140 | | | |
| Ala | Asp | Thr | Leu | Gly | Ser | Ser | Leu | Arg | Gln | Leu | Asn | Gln | Val | His | Thr |
| 145 | | | | | 150 | | | | | 155 | | | | | 160 |
| Arg | Lys | Val | Pro | Ala | Asp | Ile | Thr | Lys | Leu | Val | Thr | Phe | Ile | Val | His |
| | | | | 165 | | | | | 170 | | | | | 175 | |
| Ala | Phe | Gln | His | Leu | Lys | Glu | Trp | Ala | Thr | Trp | Ala | Asp | Glu | Gly | Tyr |
| | | | | 180 | | | | | 185 | | | | | 190 | |
| Glu | Pro | Glu | Glu | Val | Pro | Ser | Leu | Thr | Glu | Ala | Leu | Gln | His | Val | Pro |
| | | | 195 | | | | | 200 | | | | | 205 | | |
| Val | Ala | Val | Tyr | Trp | Thr | Ile | Ala | Ala | Ile | Val | Ala | Ser | Thr | Gly | Asn |
| | | | 210 | | | | | 215 | | | | | 220 | | |
| Leu | Val | Gly | Val | Ser | Thr | Tyr | Asn | Leu | Gln | Gly | Tyr | Ile | Asp | Arg | Leu |
| 225 | | | | | 230 | | | | | 235 | | | | | 240 |
| Asp | Glu | His | Val | Thr | Lys | Leu | Ala | Glu | Gln | Leu | Asn | Ser | Cys | Lys | Leu |
| | | | | 245 | | | | | 250 | | | | | 255 | |
| Gln | Ile | Gly | His | Val | Asp | Asp | Tyr | Phe | Asn | Arg | Arg | Lys | Ile | Phe | Asp |
| | | | | 260 | | | | | 265 | | | | | 270 | |

Figure 10

```
Lys Pro Lys Asp Ile Val Asp Leu Leu Lys Ala Leu Ile His Arg Asn
        275                 280                 285
Gly Ala Gln Gly Pro Gln Ile Phe Glu Gly Gly Val Ile Val Lys Gln
        290                 295                 300
Gly Leu Glu Val Phe Arg Gln Lys His Val Leu Leu Phe Ile Ser Gly
305                 310                 315                 320
Leu Asn Ser Ile Val Asp Glu Ile Leu Leu Asn Ser Ile Tyr Asn
                325                 330                 335
Arg Leu Gln Asp Asn Pro Thr Glu Val Ile Lys Gly Phe Lys Lys Glu
                340                 345                 350
Asp Phe Lys Ile Leu Trp Val Pro Met Val Asp Arg Trp Asp Glu Ala
            355                 360                 365
Ser Arg Glu Gln Tyr Leu Asn Thr Trp Lys Arg Gly Ile Lys Trp Tyr
        370                 375                 380
Ile Val Glu Tyr Phe Phe Glu Leu Pro Gly Arg Arg Ile Ile Thr Asp
385                 390                 395                 400
Pro Glu Arg Leu Gly Tyr Glu Gly Asn Pro Ile Ile Pro Val Phe Asn
                405                 410                 415
Pro Gln Gly Met Leu Thr Asn Asp Asn Ala Met Asp Leu Ile Phe Gln
                420                 425                 430
Trp Gly Ile Asp Ala Phe Pro Phe Arg Lys Ser Asp Gly Ile Asp Leu
            435                 440                 445
Thr Leu Lys Trp Lys Trp Leu Trp Asp Ile Ile Lys Lys Ala Thr Pro
        450                 455                 460
Gly Leu Gln Val Lys Val Asp Arg Tyr Ile Phe Ile Phe Gly Ser Thr
465                 470                 475                 480
Asn Asn Lys Trp Ile Gln Asp Phe Thr Ile Glu Leu Asp Lys Leu Lys
                485                 490                 495
Arg Asn Glu Thr Val Lys Arg Ala Asp Val Ile Ile Glu Gln Tyr Gln
            500                 505                 510
Leu Gly Lys Asp Asp Pro Asn Arg Val Pro Ser Phe Trp Met Gly Val
            515                 520                 525
Glu Arg Lys Lys Gln Asn Lys Lys His Gln Glu Ala Val Asp Cys Glu
        530                 535                 540
Ile Gln Gly Ile Val Lys Ser Leu Phe Cys Leu Lys Arg Asp Pro Gln
545                 550                 555                 560
Gly Trp Val Ile Leu Ser Lys Gly His Asn Ile Lys Leu Leu Gly His
                565                 570                 575
Gly Glu Ala Val Tyr Gln Thr Val Val Glu Phe Pro Asn Trp Lys Glu
            580                 585                 590
Lys Val Leu Glu Arg Glu Gly Phe Asp Ile Ala Phe Lys Glu Tyr Tyr
        595                 600                 605
Asp Ile Lys Ala Lys Glu Ile Ser Ala Arg Gln Pro Cys Glu Ile Ile
        610                 615                 620
Asn Val Asp Ser Tyr Ser Ala Asn Val Ile Ala Thr Ile Thr Cys Pro
625                 630                 635                 640
Asn Pro Met Cys Gly Arg Val Met Glu Val Thr Ser Val Asn Tyr Lys
```

Figure 10 (continued)

```
                    645                 650             655
        Cys Cys His Ser Asp Ala Pro Asn Gly Phe Gly Ile
                660                 665
```

Figure 10 (continued)

```
<210> SEQ ID-NO:7
<211> 685
<212> PRT
<213> Pisum sativum

<220>
<221> SOURCE
<222> 1..685
<223> /mol_type="protein"
      /organism="Pisum sativum"

<400> 7
Met Ser Phe Ser Asn Ser Ala Ala Ala Thr Gly Thr Leu Val Gln
1               5                   10                  15
His Gly Gly Asn Ala Thr Asn Asn Asn Ser Leu Ile Gln Lys Asn Ala
                20                  25                  30
Thr Ser Pro His Ser His His Lys Ala Asn Asn Tyr Leu Pro Asn Pro
                35                  40                  45
Phe Glu Leu His Asp Ser Gln Ile Leu Asp Lys Val Tyr Leu Thr His
        50                  55                  60
Val Thr Asp Asp Gln Phe Cys Asp Thr Asp Ile Ile Phe Asp Leu Val
65                  70                  75                  80
Ser Thr Leu Val Leu Gln Thr Asn Thr Gln Ile Pro Val Thr Gly Phe
                    85                  90                  95
Lys Pro Asp Phe Pro Thr Leu Lys Leu Ile Ser Cys Gln Met Ile Thr
                100                 105                 110
Thr Arg Ser Ala Ala His Cys Val His Gln Thr Thr Leu Trp Ile Leu
            115                 120                 125
Gln Asn Leu Arg Ser Tyr Ser Trp Asp Ala Lys Ala Leu Ile Thr Leu
        130                 135                 140
Ala Ala Phe Thr Leu Glu Tyr Gly Asn Tyr Leu His Leu Thr Arg Val
145                 150                 155                 160
Thr Ala Thr Asp Pro Ile Gly Asn Ser Leu Arg Gln Leu Asn Gln Ile
                165                 170                 175
Gln Thr Arg Asn Ile Ser Thr Asp Ile Thr Glu Leu Val Ser Phe Ile
                180                 185                 190
Val His Gln Leu Leu His Leu Lys Glu Trp Ala Thr Trp Ser Ala Glu
            195                 200                 205
Gly Tyr Asp Pro Glu Asp Val Pro Ala Leu Thr Glu Ala Leu Gln Glu
        210                 215                 220
Ile Pro Val Phe Val Tyr Trp Thr Ile Ala Ser Ile Val Ala Ser Thr
225                 230                 235                 240
Gly Asn Leu Val Gly Val Ser Asp Tyr Lys Leu Ser Glu Tyr Arg Glu
                245                 250                 255
Arg Leu Ser Gly Ile Val Gln Lys Leu Val Val His Leu Asn Asn Cys
            260                 265                 270
Lys Leu Gln Ile Ser Tyr Ile Asp Asp Leu Phe Asn Arg Lys Lys Ile
```

Figure 11

```
                   275                     280                     285
    Phe Asp Lys Pro Lys Asp Ile Val Asp Cys Leu Lys Ala Leu Ile His
        290                     295                     300
    Arg Asn Gly Thr Asp Ser Pro Gln Ile Tyr Glu Gly Ala Ile His Val
    305                     310                     315                 320
    Lys Thr Gly Leu Glu Val Phe Arg Asn Lys His Val Leu Val Phe Ile
                        325                     330                     335
    Ser Ser Leu Asp Ser Ile Glu Asp Glu Ile Ser Leu Leu Asn Ser Ile
                        340                     345                 350
    Tyr Glu Arg Leu Gln Glu Asn Ser Lys Glu Ser Ile Lys Gly Phe Lys
                355                     360                     365
    Lys Glu Asp Phe Lys Ile Leu Trp Ile Pro Ile Val Asn Asn Trp Asp
        370                     375                     380
    Asp Ile Arg Lys Glu Arg Phe Arg Ala Leu Lys Ser Gly Ile Lys Trp
    385                     390                     395                 400
    Tyr Ala Val Glu Tyr Phe Tyr Glu Leu Pro Gly His Arg Ile Ile Thr
                        405                     410                     415
    Asp Pro Glu Arg Ile Gly Tyr Ile Gly Asn Pro Ile Ile Pro Val Phe
                        420                     425                     430
    Asn Pro Gln Gly Tyr Ile Thr Asn Ile Asp Ala Met Asp Leu Ile Phe
                        435                     440                     445
    Gln Trp Gly Ile Asp Ala Phe Pro Phe Arg Lys Ser Asp Gly Ile Asp
                    450                     455                     460
    Leu Thr Leu Lys Trp Lys Trp Leu Trp Asp Val Ile Lys Lys Ala Thr
    465                     470                     475                 480
    Pro Gly Leu Gln Val Lys Gly Asp Arg Tyr Ile Phe Ile Tyr Gly Gly
                        485                     490                     495
    Thr Asn Asn Lys Trp Ile Gln Asp Phe Thr Leu Glu Leu Glu Lys Ile
                        500                     505                     510
    Lys Arg His Glu Ile Leu Lys Arg Ala Asp Val Ile Ile Glu Asn Tyr
                515                     520                     525
    Gln Leu Gly Lys Glu Asp Pro Asn Arg Val Pro Ser Phe Trp Ile Gly
            530                     535                     540
    Val Glu Arg Lys Lys Gln Asn Lys Lys His Gln Glu Ala Leu Asp Cys
    545                     550                     555                 560
    Glu Ile Gln Asp Ile Val Lys Ser Leu Phe Cys Leu Lys Arg Asp Pro
                        565                     570                     575
    Gln Gly Trp Ile Ile Leu Ser Lys Gly Gln Asn Ile Lys Leu Leu Gly
                        580                     585                     590
    His Gly Glu Pro Ala Tyr Gln Thr Leu Ala Glu Phe Gln Asn Trp Lys
                595                     600                     605
    Asp Arg Val Leu Glu Lys Glu Gly Phe Asp Ile Ala Phe Lys Glu Tyr
            610                     615                     620
    Tyr Glu Met Lys Ala Lys Glu Leu Ser Gly Arg Gln Pro Cys Glu Val
    625                     630                     635                 640
    Val Asn Val Asp Thr Tyr Ser Ser Asn Val Ile Ala Thr Ile Ala Cys
                        645                     650                     655
```

Figure 11 (continued)

```
Pro Asn Pro Met Cys Gly Arg Val Met Glu Val Ser Ser Ala His Tyr
            660                 665                 670
Lys Cys Cys His Arg Asp Glu Pro Asn Asn Phe Gly Val
            675                 680                 685
```

Figure 11 (continued)

```
<210> SEQ ID-NO:8
<211> 684
<212> PRT
<213> Vicia faba

<220>
<221> SOURCE
<222> 1..684
<223> /mol_type="protein"
      /organism="Vicia faba"

<400> 8
```

| | | | | | | | | | | | | | | |
|---|---|---|---|---|---|---|---|---|---|---|---|---|---|---|
| Met | Ser | Phe | Ser | Asn | Ser | Pro | Ala | Ala | Thr | Gly | Thr | Leu | Val | Gln |
| 1 | | | | 5 | | | | | 10 | | | | | 15 |
| His | Gly | Gly | Asn | Gly | Thr | Asn | Asn | Ser | Leu | Ile | Gln | Lys | Thr | Ala | Thr |
| | | | 20 | | | | | 25 | | | | | 30 | |
| Ser | Ser | His | Pro | His | His | Lys | Ala | Asn | Asn | Tyr | Leu | Pro | Asn | Pro | Phe |
| | | | 35 | | | | | 40 | | | | | 45 | |
| Glu | Leu | His | Asp | Ser | His | Ile | Leu | Asp | Lys | Val | Tyr | Leu | Thr | His | Val |
| | | 50 | | | | | 55 | | | | | 60 | | |
| Thr | Asp | Asp | Glu | Phe | Cys | Asp | Thr | Asp | Ile | Ile | Phe | Asp | Leu | Val | Ser |
| 65 | | | | | 70 | | | | | 75 | | | | | 80 |
| Thr | Leu | Ile | Leu | Gln | Ser | Asn | Thr | Gln | Ile | Pro | Val | Thr | Gly | Phe | Lys |
| | | | | 85 | | | | | 90 | | | | | 95 | |
| Pro | Asp | Phe | Pro | Thr | Leu | Lys | Leu | Ile | Ser | Cys | Gln | Met | Ile | Thr | Thr |
| | | | | 100 | | | | | 105 | | | | | 110 | |
| Arg | Ser | Val | Ala | His | Cys | Val | His | Gln | Thr | Thr | Leu | Trp | Ile | Leu | Gln |
| | | | 115 | | | | | 120 | | | | | 125 | | |
| Asn | Leu | Arg | Ser | Tyr | Ser | Trp | Asp | Ala | Lys | Ala | Leu | Ile | Thr | Leu | Ala |
| | | 130 | | | | | 135 | | | | | 140 | | | |
| Ala | Phe | Thr | Leu | Glu | Tyr | Gly | Asn | Tyr | Leu | Gln | Leu | Asn | Arg | Val | Thr |
| 145 | | | | | 150 | | | | | 155 | | | | | 160 |
| Ala | Thr | Asp | Pro | Ile | Gly | Asn | Ser | Leu | Arg | Gln | Leu | Asn | Gln | Ile | Gln |
| | | | | 165 | | | | | 170 | | | | | 175 | |
| Thr | Arg | Lys | Ile | Ser | Thr | Asp | Ile | Pro | Glu | Leu | Val | Asn | Phe | Ile | Val |
| | | | 180 | | | | | 185 | | | | | 190 | | |
| His | Lys | Leu | Leu | His | Leu | Lys | Glu | Trp | Ala | Ala | Trp | Ser | Ala | Glu | Gly |
| | | | 195 | | | | | 200 | | | | | 205 | | |
| Tyr | Asp | Pro | Glu | Asp | Val | Pro | Ala | Leu | Thr | Glu | Ala | Leu | Gln | Glu | Ile |
| | | 210 | | | | | 215 | | | | | 220 | | | |
| Pro | Val | Phe | Val | Tyr | Trp | Thr | Ile | Ala | Ser | Ile | Val | Ala | Ser | Thr | Gly |
| 225 | | | | | 230 | | | | | 235 | | | | | 240 |
| Asn | Leu | Val | Gly | Val | Ser | Asp | Tyr | Asn | Leu | Ser | Glu | Tyr | Arg | Glu | Arg |
| | | | | 245 | | | | | 250 | | | | | 255 | |
| Leu | Ser | Gly | Ile | Val | Gln | Lys | Leu | Val | Val | His | Leu | Asn | Asn | Cys | Lys |
| | | | 260 | | | | | 265 | | | | | 270 | | |
| Leu | Gln | Ile | Ser | Tyr | Ile | Asp | Asp | Leu | Phe | Asn | Arg | Arg | Lys | Ile | Phe |

Figure 12

```
                    275                         280                         285
Asp Lys Pro Lys Asp Ile Val Asp Cys Leu Lys Ala Leu Ile His His
                290                         295                         300
Asn Gly Ala Asp Ser Pro Gln Ile Tyr Glu Gly Ala Ile His Val Lys
305                         310                         315                         320
Thr Gly Leu Glu Val Phe Arg His Lys His Val Leu Met Phe Ile Ser
                    325                         330                         335
Ser Leu Asp Ser Ile Glu Asp Glu Ile Ser Leu Leu Asn Ser Ile Tyr
                340                         345                         350
Glu Arg Leu Gln Glu Asn Ser Lys Glu Ser Ile Lys Gly Phe Lys Lys
                355                         360                         365
Glu Asp Phe Lys Ile Leu Trp Ile Pro Ile Val Asn Asn Trp Asp Asp
                370                         375                         380
Ile Arg Lys Glu Arg Phe Arg Ala Leu Lys Ser Gly Ile Lys Trp Tyr
385                         390                         395                         400
Ala Val Glu Tyr Phe Tyr Glu Leu Pro Gly His Arg Ile Ile Thr Asp
                    405                         410                         415
Pro Glu Arg Ile Gly Tyr Ile Gly Asn Pro Ile Ile Pro Val Phe Asn
                420                         425                         430
Pro His Gly Tyr Ile Thr Asn Ile Asp Ala Met Asp Leu Ile Phe Gln
                435                         440                         445
Trp Gly Ile Asp Ala Phe Pro Phe Arg Lys Ser Asp Gly Ile Asp Leu
                450                         455                         460
Thr Phe Lys Trp Lys Trp Leu Trp Asp Val Ile Lys Lys Ala Thr Pro
465                         470                         475                         480
Gly Leu Gln Val Lys Gly Asp Arg Tyr Ile Phe Ile Tyr Gly Gly Thr
                    485                         490                         495
Asn Asn Lys Trp Ile Gln Asp Phe Thr Leu Glu Leu Glu Lys Ile Lys
                500                         505                         510
Arg His Glu Thr Leu Lys Arg Ala Asp Val Ile Ile Asp Asn Tyr Gln
                515                         520                         525
Leu Gly Lys Asp Asp Pro Asn Arg Val Pro Ser Phe Trp Ile Gly Val
                530                         535                         540
Glu Arg Lys Lys Gln Asn Lys Lys His Gln Glu Ala Val Asp Cys Glu
545                         550                         555                         560
Ile Gln Asp Ile Val Lys Ser Leu Phe Cys Leu Lys Arg Asp Pro Gln
                    565                         570                         575
Gly Trp Val Ile Leu Ser Lys Gly Gln Asn Ile Lys Leu Leu Gly His
                580                         585                         590
Gly Glu Pro Ala Tyr Gln Thr Leu Ala Glu Phe Gln Asn Trp Lys Asp
                595                         600                         605
Arg Val Leu Glu Lys Glu Gly Phe Asp Ile Ala Phe Lys Glu Tyr Tyr
                610                         615                         620
Glu Met Lys Ala Lys Glu Leu Ser Gly Arg Glu Pro Cys Glu Val Val
625                         630                         635                         640
Asn Val Asp Thr Tyr Ser Ser Asn Val Ile Ala Thr Ile Ala Cys Pro
                    645                         650                         655
```

Figure 12 (continued)

```
Asn Pro Met Cys Gly Arg Val Met Glu Val Ser Ser Val His Tyr Lys
            660                 665                 670
Cys Cys His Arg Asp Glu Pro Asn Asn Phe Gly Val
        675                 680
```

Figure 12 (continued)

```
<210> SEQ ID-NO:9
<211> 238
<212> PRT
<213> GFP fusion vector pGUG

<220>
<221> SOURCE
<222> 1..238
<223> /mol_type="protein"
     /organism=aequorea victoria
<400> 9
```

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Ser Gly Glu
            20                  25                  30
Gly Glu Gly Asp Ala Thr Tyr Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Thr Tyr Gly Val Gln Cys Phe Ser Arg Tyr Pro Asp His Met Lys Gln
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr His Gly Met Asp Glu Leu Tyr Lys
225                 230                 235

Figure 13

```
<210> SEQ ID-NO: 10
<211> 239
<212> PRT
<213> Venus

<220>
<221> SOURCE
<222> 1..239
<223> /mol_type="protein"

<400> 10
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Leu Ile
                35                  40                  45
Cys Thr Thr Gly Lys Leu Pro Val Pro Trp Pro Thr Leu Val Thr Thr
            50                  55                  60
Phe Gly Tyr Gly Leu Gln Cys Phe Ala Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
        130                 135                 140
Asn Tyr Asn Ser His Asn Val Tyr Ile Thr Ala Asp Lys Gln Lys Asn
145                 150                 155                 160
Gly Ile Lys Ala Asn Phe Lys Ile Arg His Asn Ile Glu Asp Gly Gly
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Tyr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys
225                 230                 235
```

Figure 14

ARTIFICIAL FORISOME BODY WITH SEO-F FUSION PROTEINS, PLANT OR YEAST CELLS COMPRISING VECTORS WHICH CODE FOR THESE PROTEINS, AS WELL AS VECTORS WHICH CODE FOR SEO-F FUSION PROTEINS

The present invention relates to artificial forisome bodies having properties useful protein-chemistry, plant cells and yeast cells with a combination of vectors that enable formation and isolation of said forisome bodies in the cell, and novel vectors encoding SEO-F fusion proteins.

Forisomes are plant protein bodies (mechanoproteins), which are found exclusively in the phloem of plants of the Fabaceae family (legumes). They are located in the sieve plates of the phloem system. When the phloem is wounded, forisomes undergo a calcium-dependent conformational change that converts them from a condensed state to a thickened, dispersed state that allows them to plug the sieve elements and prevent the loss of valuable sugar molecules. Forisomes exist as fibrillar substructures packed into large, compact bundles. In vitro, divalent cations, pH changes, or electrical stimuli can trigger forisomes to undergo numerous ATP-independent repeatable cycles of contractions and alternating expansions.

A forisome is comprised of several million subunits. These subunits are homologous proteins that, according to their function, are named "Sieve Element Occlusion by Forisomes" (SEO-F). The thesis by Gundula Noll (2005) describes expression of several genes that code for these proteins using bacterial expression vectors. It was determined that in Medicago truncatula at least four subunits (SEO-F1 to SEO-F4) exist (G. Noll et al., Plant Mol. Biol. 65:285-294 (2007), HC Pelissier et al., Plant Cell Physiol. 49:1699-1710 (2008)). All four subunits have meanwhile been sequenced; their sequences (SEQ-ID NO: 1-4) are shown in FIGS. 1-4. The sequences of SEO-F1 proteins of the species Dipteryx panamensis, Lotus japonicus, Pisum sativum and Vicia faba (SEQ-ID NO: 5-8) are shown in FIGS. 9-12. In plants, the different SEO-F proteins assemble to forisome protein bodies. Expression of the corresponding genes in foreign organisms (tobacco plants, yeast) has meanwhile demonstrated that in Medicago truncatula each of the two sub-units, namely SEO-F1 and SEO-F4, assemble into homomeric artificial forisomes in the absence of other subunits, see G. Noll et al., Bioengineered Bugs 2:2, 1-4 (2011), 2011 Landes Bioscience. The SEO-F2 subunit, in contrast, cannot assemble into homomeric forisomes, but can co-assemble both with the SEO-F1 subunit as well as with the SEO-F4 subunit.

Some SEO-F fusion proteins have previously been generated for analytical purposes. Accordingly, G. Noll performed forisome gene-enzyme coupling in the context of her dissertation (2005) for the purpose of producing antibodies in E. coli. However, formation of forisome bodies was hereby not detectable. H. C. Pelissier et al. describe loc. cit. a fusion protein consisting of a forisome subunit and the green fluorescent protein (GFP) that allowed them to demonstrate the assembly of this subunit to a forisome body in transgenic plants in which the fusion protein was stored. In Appl. Microbiol. Biotechnol. (2010) 88:689-698 (2010) B. Müller et al. describe the preparation of four fusion protein vectors that encode one of the MtSEO1 to MtSE04 genes of Medicago truncatula and the Venus yellow fluorescent protein gene. The fusion protein was successfully expressed in epidermal cells of N. benthamiana; when the respective MtSEO gene was co-expressed with MtSEO-F1 or MtSEO-F4, protein complexes were formed that resembled a forisome body but had a different phenotypes. Using the same experimental approach, in the case of MtSEO-F2 and MtSEO-F3 protein was detectable that was localized in the cytoplasm only. In addition, MtSEO-F1/MtSEO-F1venus and MtSEO-F4/MtSEO-F4venus were coexpressed in yeast to demonstrate the possibility of producing such artificial forisome bodies in larger quantities. Furthermore, large quantities of artificial forisomes can be produced by single expression of MtSEO-F1 or MtSEO-F4.

In the past decades, great strides have been made in protein biochemistry, however the purification of recombinant proteins often still presents a substantial challenge, for example for membrane-associated or toxic proteins. In particular with enzymes, it is often observed that the quantity of the enzyme and/or its activity is not within a desirable range making the cost of the assay or the like unreasonably high because of the amount of enzyme required. The expression of recombinant proteins itself may in turn be problematic; some of these proteins may not be folded correctly in the expression organism, or deposited in an inactive form as inclusion bodies within the cell. A further requirement for production is the re-usability of enzymes, which is often accomplished by immobilization on support materials (agarose, nylon). This immobilization often results in strongly reduced enzyme activities, leading to disproportionately high costs of the subsequent assays. Purification of polyclonal antibodies in particular, which is usually performed by chromatographic methods, also remains to be improved. The inventors have therefore set themselves the task to remedy this situation by providing proteins that, on the one hand, can be produced with reasonable effort and, on the other hand, have a structure or form that facilitates the use of these proteins for the afore-mentioned purposes, and/or improves the results obtained with their use compared to results obtained with known proteins or other materials previously used for this purpose.

To solve this object, the invention proposes to provide modified forisomes. They can improve and simplify many areas of protein chemistry by the biochemically active structures that are contained in the form of fusion proteins therein. When the fusion introduces enzymatic functions to the forisomes, the forisomes can serve as carrier proteins to which the enzymes are immovably coupled, thus circumventing attachment to an external matrix. The forisome may also provide a protective function to the foreign coupled protein in the context of recombinant protein production, e.g., by simplifying their purification: The foreign protein can be easily isolated in the form of forisomes and, if needed, subsequently excised by means of appropriate protease cleavage sites and corresponding proteolytic enzymes. When antigenic structures are introduced into the forisome by fusion, these structures can be employed for purification of antibodies. In addition, by selectively varying their binding properties or by changing their conformation, the bodies according to the invention may be used for micromechanical purposes.

From the above-cited work in combination with the analysis of the SEO-F genes and proteins, it is known that a fusion protein consisting of a SEO-F1 or SEO-F4 protein, a fluorescent tag, and a corresponding native protein are capable of forming forisome bodies. However, the inventors of the present invention found that the assembly of forisomes from, or with, fusion proteins containing any SEO-F unit fused to any protein is not possible. They were nevertheless able to produce artificial forisome bodies containing foreign proteins that were suitable for the purpose of the invention. These forisome bodies can be expressed in yeast, thus allowing large production of forisomes. The authors were successful because it was shown that SEO-F proteins and/or fragments thereof may be combined with either the C-terminus or the N-terminus of a variety of proteins and, optionally, of peptides, whereby forisomes are formed, provided one of the following conditions is met.

The object of the invention is accordingly achieved by providing artificial forisome bodies comprising a fusion protein of at least one SEO-F protein or an at least 50-amino acid portion thereof, and at least one additional protein or peptide, wherein (a) the additional protein or peptide has a mass of at most 30 kDa, preferably of at most 25 kDa, and/or
(b) the forisome body further comprises an unfused, often native SEO-F protein or a form of said protein having C-terminal deletions of up to approximately 50, in particular of up to 45, and preferably of up to 43 amino acids and/or N-terminal deletions of up to 13 amino acids, wherein the unfused SEO-F protein has the property of forming homomeric forisome bodies in the absence of additional SEO-F proteins, or
(c) the additional protein or peptide is a portion of a second SEO-F protein, with the proviso that one of the two SEO-F proteins in its unfused form is capable of forming homomeric forisome bodies, and the fusion protein is comprised of an N-terminal SEO-F protein portion and a C-terminal SEO-F protein portion, wherein the fusion is within a region that is identical or approximately identical in both SEO-F proteins and is located within an identical or substantially identical region of the proteins relative to a region that is relevant for their function, so that the fusion protein represents a complete SEO-F protein, wherein however up to approximately 50 amino acids, in particular up to 45 amino acids, and preferably up to 43 amino acids of the C-terminus and/or 13 amino acids of the N-terminus may be deleted.

Of course, the present invention also encompasses forisome bodies that fulfill more than one of the conditions (a), (b) and (c).

BRIEF DESCRIPTION OF THE DRAWINGS

Embodiments of the invention will now be described by way of example with reference to the accompanying drawings.

FIGS. 1-4 show sequences (SEQ-ID NO: 1-4) of the four subunits (SEO-F1 to SEO-F4) in *Medicago truncatula*.

FIGS. 9-12 show the sequences of SEO-F1 proteins of the species *Dipteryx panamensis, Lotus japonicus, Pisum sativum* and *Vicia faba* (SEQ-ID NO: 5-8).

FIGS. 13 and 14 show the sequences of an SEO-F peptide fused to a GFP protein (FIG. 13 and SEQ ID NO: 9) or to a Venus protein (FIG. 14 and SEQ ID NO: 10).

Figure 5:
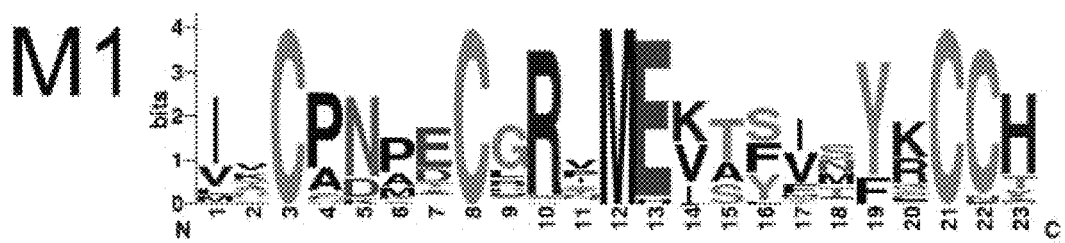
FIG. 5 shows a particular sequence motif as described in the present application.

As already mentioned above, forisome bodies assembled from the combination of fusion proteins MtSEO-F1venus and MtSEO-F4venus with corresponding native proteins such as MtSEO-F1/MtSEO-F1venus and MtSEO-F4/MtSEO-F4venus are known from the prior art. These shall be excluded from the scope of the patent. They were produced for the purpose of forisome detection, while the present invention is in no way aimed at detecting forisomes, but at solving specific problems that occur in protein chemistry. Therefore, all such forisome bodies shall fall outside the scope of the patent that were generated from or with fusion proteins having a SEO-F protein or SEO-F peptide fused to a GFP protein (see FIG. 13 and SEQ ID NO:9) or to a Venus protein (see FIG. 14 and SEQ ID NO:10) or a portion thereof, or fused to a (artificial) variant thereof, provided the fusion protein is fluorescent, optionally by use of excitation light (such as blue or ultraviolet light). Those forisome bodies shall also not fall within the scope of the patent that are constructed to contain fusion proteins fused to other fluorescent or otherwise visually detectable peptides and proteins, e.g., chemiluminescent proteins, provided said fusion proteins are not biochemically active or activatable in the sense hereinafter defined. In the broadest sense, this may optionally apply to any forisome body assembled from or comprising fusion proteins containing protein components of non-SEO-F molecules that serve no other purpose, or are generally not intended to serve another purpose than detecting the presence of the desired fusion. The exceptions named of course extend to all products of this invention that contain the above-mentioned forisome bodies or with which said forisome bodies and/or corresponding fusion proteins can be produced.

The invention is aimed at the production of forisome fusion proteins that confer artificial biochemical activity or activatability or altered mechanical properties to the forisomes. Therefore, the additional peptide or protein is selected from the group of biochemically active or activatable proteins or peptides, and portions of a second SEO-F protein.

The term "biochemically active or activatable proteins or peptides" according to the invention includes, among others, any protein involved in metabolism such as enzymes—due to their biocatalytic effects—, any protein capable of eliciting an immune reaction, or proteins that are therapeutically beneficial such as in particular antibodies and antigens, all peptides or proteins having binding sites for foreign proteins or peptides, and other biotechnologically useful proteins and peptides. The term "biotechnologically useful" according to the invention includes for example any protein and peptide whose synthesis may be of significance for medical applications or diagnostic methods. Several proteins can be immobilized due to their affinity reaction with substrate-bound biological or biochemically-produced materials in order to enable their re-usability. Such proteins or peptides are also included in the term "biotechnologically useful." Not covered by the term on the other hand are proteins or peptides that are (exclusively) designed to detect the fusion protein formation such as optically detectable, in particular fluorescent proteins, especially when said proteins or peptides do not possess biocatalytic activity or any other of the above-mentioned properties.

The inventors have found that forisome bodies can generally always be assembled in yeast when the fusion proteins of the invention are co-expressed with an unfused, for example native SEO-F protein, provided said SEO-F proteins has the property of forming homomeric forisome bodies in the absence of other SEO-F proteins, see condition (b). This is likely due to the fact that because of the presence of homomer-forming SEO-F molecule, the number and characteristics of the structures relevant for assembly is relatively high.

Surprisingly, however, the inventors have found that the above-defined fusion proteins assemble to forisome bodies even in the absence of said unfused SEO-F proteins in yeast when the proportion of foreign protein does not exceed a certain size. The inventors have found that this occurs when the non-SEO-F-portion has a mass of at most 30 kDa. It is more advantageous to limit the size to approximately 25 kDa (condition (a)). The forisome bodies thus obtainable are somewhat thinner and more fibrous, but can still be purified.

In regards to the definition of artificial forisomes in provision (c) it must be mentioned that in the context of the invention it was determined that SEO-F fusion products having all required properties of a SEO-F protein can be produced artificially. This requires that at least a portion of the fusion protein is derived from a SEO-F protein that is capable of forming homomeric forisomes. It is believed that in these proteins the structures that are required for assembly and thus contribute to the formation of forisomes are more pronounced. The aforementioned possibility that a certain deletion, which can be more extensive in the C-terminal region than in the N-terminal region, is, according to inventors preliminary opinion without being absolutely bound thereto, due to the fact that the structures relevant for assembly are not located within these regions.

The inventors discovery that according to conditions (c) artificial SEO-F proteins can be obtained that have the ability of assembling to homomeric forisomes, i.e., without additional, for example unfused protein, enables the preparation of forisomes having assembly properties that can be appropriately controlled, e.g. increased. In this way the mechanical properties of such forisomes can be adjusted to the desired applications. For example, the conditions ($Ca^{2+}$ concentration and/or pH and/or electrical stimuli) required for conformational changes can be varied so that the forisomes can also be technically used under conditions that are not able capable of inducing conformational changes in native forisomes.

According to the invention, the fusion protein may contain the additional protein C-terminally i.e. based on the cloning vector and the DNA reading frame, "upstream", or N-terminally, i.e. based on the cloning vector and the DNA reading frame "downstream."

Particular advantages of using the present invention can be achieved in the following areas:

a) Enzyme immobilization is used for industrial enzymes as it offers the advantage of re-using enzymes and minimizing contaminations in the enzyme product. However, the carrier material generally reduces the stability and activity of enzymes compared to their soluble forms. To date, enzyme immobilization is conducted mainly by adsorption, entrapment, cross-linking, or covalent binding of the enzyme to substrate materials. Disadvantages of immobilization methods include for example insufficient binding of the enzyme following adsorption and inclusion, the use of toxic chemicals for cross-linking, and blockage of essential functional amino acids groups when covalent bonds are introduced. The support materials used to date are synthetic polymers such as acrylic resins, hydrogels and silica, smart polymers such as PNIPAM, or biopolymers such as agarose, cellulose, starch, and chitosan. For example, glucose-6-phosphate dehydrogenase immobilized to agarose beads with an activity of 1000-1750 Units/gram agarose is commercially available. The purification of the enzyme, and the subsequent coupling of the enzyme to the carrier material thereby represent two separate steps, wherein the enzyme activity after immobilization is greatly reduced.

b) Depending on the properties of the protein, expression of recombinant proteins may be problematic. For example toxic proteins affect the vitality of the expression organism and reduce the amount of recombinant protein produced. Other proteins are not properly folded or deposited as inclusion bodies in inactive forms within the cell. Other problems may occur during purification of the recombinant protein. For example, the isolation of membrane proteins is complicated by their interaction with membrane components, or proteins may be degraded during the purification process. Furthermore, the process of protein purification is usually very expensive and often requires the use of large amounts of environmentally harmful chemicals. In practice, even in industrial manufacturing process, the purification consists of multiple steps. The steps involved include precipitation, filtration, or chromatographic methods. The most important criteria of these methods are the purification efficiency, cost efficiency, and biological sustainability. For example, precipitation is very cost-effective, but delivers a low degree of purity and requires use of large amounts of chemicals, while filtration or chromatographic methods are often very expensive. For this reason, the development of new purification methods that increase the purity of the product, reduce costs, and minimize the use of chemicals are of great interest to the industry.

c) Polyclonal antibodies are generated by injecting animals with respective antigens (proteins or peptides). Several weeks later, the polyclonal serum may be harvested from the blood of the animal. For the generation of monoclonal antibodies, plasma cells from spleen or lymph nodes of immunized animals are isolated, fused with tumor cells, and grown in sterile culture. After several rounds of selection, hybridoma cultures can be obtained that originate from a single cell and secrete the desired monoclonal antibody. In particular with polyclonal antibodies, more rarely with monoclonal antibodies, the serum contains not only the desired antibodies but also undesired antibodies (e.g., keratin antibodies) and/or substances that interfere with detection (e.g., proteins that are similar to the antigen used, or proteins that aggregate and interfere with detection methods.) These substances must be removed from the desired antibody. To date, this has been accomplished by chromatographic methods wherein the antigen is bound to a column matrix. The matrix is subsequently incubated with the "impure" antibody solution, allowing the specific antibodies to bind to the antigen, and thus to the matrix. After the matrix is washed, the antibodies are eluted from the column (e.g., by a solution with an acidic pH.) A simplification of this laborious method and increased efficiency is extremely desirable.

d) The advantages of the invention, however, are not limited only to the manufacture and the properties of foreign proteins; they can be advantageously used in the field of forisomes itself: As mentioned above, forisomes are plant mechanoproteins that can be employed e.g., as control modules in microfluidic systems due to their calcium or pH-inducible conformational changes. These properties allowed A. Q. Shen et al. in Smart Struct. Syst. 2, 225-235 (2006) and K. Uhlig et al. in J. Microelektromech. Sys. 17, 1322-1328 (2008) to demonstrate that the flux of fluorescent particles in microchannels could be controlled using forisomes integrated therein. However, targeted, permanent attachment of forisomes can only be achieved to date manually with the help of micromanipulation techniques that require a very large amount of time and effort. Thus, Shen et al. and Uhlig et al. (loc. cit.) took advantage of forisome's natural adhesion to glass. Forisomes thereby adhere to surfaces when pressed against them. However, the adhesion does not enable permanent attachment of the forisomes in a fluid stream. In addition, the strength of the forisome reaction is reduced upon their adhesion to surfaces (G. A. Noll et al., Bioeng. Bugs 2, 111-114 (2011)).

The provision of forisomes with conformational properties that can be altered by known stimuli (e.g., upon conversion from a condensed to dispersed state and vice versa at a different pH or with a different $Ca^{2+}$ concentration) is also desirable.

The inventors of the present invention succeeded in providing a material that has advantages in all four of the mentioned areas. It was thereby found that expression of fusion proteins is often possible when forisome proteins that can form homomers independently of the presence of other forisome subunits are co-expressed in the same cell. In contrast, the expression of the fusion protein alone yields usable product only when small foreign proteins are used, while in other cases forisome bodies are not formed and instead the protein is present in soluble form or deposited in the cell as "inclusion body."

When a fusion protein is co-expressed with a homomeric forisome body forming SEO-F subunit and/or a when a fusion protein of a relatively small foreign protein component is expressed, stable forisome bodies can be expressed in plants and in yeast having substantially the form of native forisomes, despite the presence of a foreign protein or peptide. Thus, the invention offers the possibility of producing individually modulatable functionalized artificial forisomes. This was surprising in itself, but also in particular the finding that the assembly of the forisome bodies did not impede the functional activity of the foreign protein. Using the example of enzymes fused to SEO-F units it was shown that the forisome bodies reduced the activity of the foreign proteins to a lesser extent than commercially applied immobilization matrices; it may be assumed that this applies to all fusion proteins, despite not having being demonstrated for a number of other proteins due to lack of quantitative comparisons.

The use of MtSEO-F1 and MtSEO-F4 is particularly preferred; however, SEO-F subunits from other sources may be used equally well.

It has been found that it is not necessary for the entire amino acid chain of a respective native SEO-F subunit to be present in the fusion protein. Instead, even a relatively small amount thereof suffices, for example, a region of approximately 60 to 250 amino acids in length, as the inventors were able to determine via fusion with fluorescent proteins. This also corresponds to the finding that the presence of homomer-forming proteins such as SEO-F1 and/or SEO-F4 determines whether forisome are formed when the foreign protein exceeds a certain size.

The SEO-F component of the fusion protein can be derived from any SEO-F subunit; preferably, it is derived from the subunits SEO-F1, SEO-F2 and SEO-F4, especially from MtSEO-F1, MtSEO-F2 and MtSEO-F4.

The coexpressed, unfused SEO F protein, if present, should be substantially or at least in large part complete in order to ensure forisome formation. The inventors have found, however, that it is not required for the entire chain of respective subunits to be present. An N-terminal deletion of at least up to 13 amino acids and/or C-terminal deletions of at least up to 43 amino acids, optionally of up to 45 and possibly up to 50 amino acids are acceptable without the forisome bodies of the present invention being adversely affected.

The forisome bodies of the present invention may be comprised of any number of subunits; generally, a species of a non-fused SEO-F subunit in combination with a species of a fusion protein is sufficient, or a species of the fusion protein alone, provided the foreign protein component does not exceed the mentioned size. The forisome bodies generally consist of from approximately $10^6$-$10^7$ individual protein chains, wherein optionally the ratio of the number of unfused SEO-F subunits to the number of fusion proteins is approximately between 4:1-1:1, depending on the type and size of the foreign protein.

Individual forisome bodies of the invention are generally comprised of only one type of fusion protein; however, they may also contain several different fusion proteins. A specific, particularly advantageous example thereof is illustrated below in point 1).

The origin of the native source of the respective forisome subunits is not significant for the invention. It was possible to produce forisome bodies according to the invention with SEO-F genes, for example, from the organisms *Dipteryx panamensis, Pisum sativum, Vicia faba, Canavalia gladiata* and *Lotus japonicus*. This suggests that it is possible to employ corresponding genes of any plants of the Fabacea family in the invention. In addition, genetically modified or synthetic SEO-F genes and/or forisomes subunits may be employed provided all of the conserved regions of genes of this plant family are preserved and/or present.

It has been suspected for some time that a sequence of four cysteines in the amino acid sequence of the various forisomes subunits greatly affects their structure and stability. These cysteines are located in the C-terminal portion of the amino acid sequence (following position 600) of all three forisomes subunits SEO-F1, F2, and SEO-SEO-F4, in each case within a highly conserved motif CPNPXCGRVMEVX-SXXYKCC (where X denotes a variable amino acid). This motif is highly conserved in all SEO genes (i.e., also in those of other plant families). The corresponding sequence motif is shown in FIG. 5. However, the inventors have shown that the presence of this region is not essential for forisomes formation: As mentioned above, it is possible to use a SEO-F-protein in form of a coexpressed unfused SEO-F protein or a fusion protein comprising two SEO-F components, having a C-terminal deletion of up to 43, possibly even up to 45 or even 50 amino acids without the inventive feature of protein chain aggregation being lost. However, when the complete sequence of a SEO-F1 or SEO-F4 is used, or at least a sequence in which at least a part or all of the said conserved motif is present, the above cysteines obviously have a significant role: It has been shown that when the mentioned cysteines are partially or completely replaced, for example by "site-directed mutagenesis," by amino acids which do not allow disulfide bond formation, e.g., glycine or alanine, the conformational states of the forisome bodies changes as follows: If the last two of said cysteines (cysteines C21 and C22 in the sequence motif) are mutated, the protein fibrils no longer assemble in all cases to forisome bodies, but may form a random fiber network. Without being bound by theory, it can therefore be assumed that the disulfide bonds between said cysteines of two SEO-F subunits are responsible for the ordered assembly of the protein fibrils. If, in contrast, at least one of the first two said cysteines (cysteines C3 and C8 in the sequence motif) is mutated, a typical forisome body is assembled upon its expression which, however, completely dissolves when calcium ions and NaHSO$_3$ are added. Calcium thereby triggers the protein fibrils to repel, while the addition of NaHSO$_3$ disrupts remaining disulfide bonds. It can therefore be assumed that the C3 and C8 cysteines are involved in the association of individual subunits to form fibers, which allows the protein to adopt its soluble form upon mutagenesis.

The fibrous bodies may have advantageous properties and are encompassed by the invention. The term "artificial forisome," as used in the present invention, is therefore intended to also encompass the fiber network in at least one embodiment of the invention.

The production of soluble forisomes-bodies as described above is particularly advantageous, as it may facilitate the purification of proteins, as shown in the examples below.

As mentioned above, the preparation of forisome bodies is preferably performed in cells of plants or yeast, with the use of yeast cells being particularly beneficial because they enable the production of large amounts of artificial forisome bodies. The invention is therefore also directed to the corresponding transformed cells. Finally, the invention also comprises novel vector constructs by means of which forisome bodies according to the invention can be produced.

The invention shall be detailed with reference to several examples that demonstrate the breadth of application of the invention on the one hand and on the other specify the individual measures that enable the expert to carry out the invention. It should therefore be clear that the above examples are not meant to be limiting.

1) Forisome Bodies with Enzyme-linked Fusion Proteins

The linking of enzymes to SEO-F proteins allows the artificial forisomes to be functionalized in such a manner that they can serve as substrates for enzymes. Enzymes may thus be immobilized. Enzyme-linked forisomes are constructed as follows: They consist of a first, optionally shortened, SEO-F subunit that is fused to an enzyme, and optionally a second SEO-F unit selected from SEO-F1 and SEO-F4, which may be deleted as described above if necessary or if desired. The enzyme may be fused to the C- or N-terminus of the fusion protein. Fusions proteins can be generated by coexpression in organisms suitable for expression such as yeast (e.g., *Saccharomyces cerevisiae*), bacteria (e.g., *Escherichia coli*) or plants (e.g., tobacco). The (co-) expression in yeast is particularly preferred. The resulting enzyme-linked forisomes are characterized by high stability. They are isolated from the expression organism (e.g., by disruption of yeast cells) and are separated from cell components, e.g., by centrifugation/density gradient centrifugation. Appropriate enzyme activity assays are used to verify the activity of the coupled enzyme. Using glucose-6-phosphate dehydrogenase as an enzyme fused to the N-terminus of a forisome subunit, a significantly higher enzymatic activity was measured in comparison to the commercially available immobilized enzyme (2700 Units/gram forisome compared to 1000-1750 U/g agarose, see FIG. 4). The enzyme was isolated directly in an immobilized form from the production organism, thereby omitting the step of substrate coupling in the enzyme production. This not only facilitates the procedure, but obviously and surprising causes an extreme increase in activity. Fusion proteins containing hexokinase and phosphoglucoisomerase that were prepared in a similar manner yielded similar results. When not only one, but two or even more fusion proteins are coexpressed, wherein the fusion partners are selected so that the reaction product of the first enzyme is a substrate for the second enzyme and its reaction product is optionally a substrate for a third protein, etc., reaction complexes can be generated that allow certain reaction pathways to take place.

In the fusion protein, the enzyme can also be bound to the C-terminus of the SEO-F protein.

2) Purification of Recombinant Proteins

Figure 7:
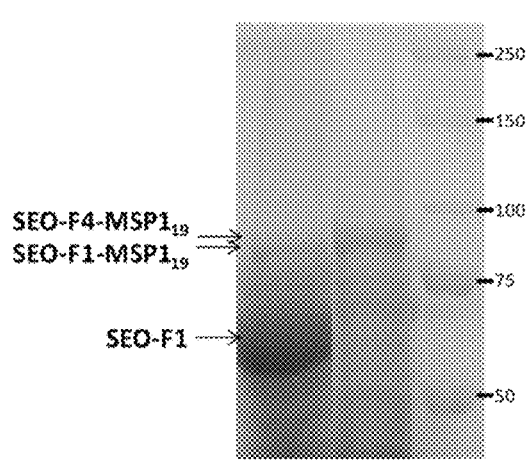
FIG. 7 illustrates immunological detection of the malaria antigen $MSP1_{19}$, successfully purified by the present invention.

As mentioned above, the artificial forisome bodies of the invention can also be used as purification systems for recombinant proteins. Said proteins are thereby fused to a SEO-F subunit and the fusion protein is optionally co-expressed with a second SEO-F subunit that is able to form homomers in the absence of other subunits, as described above, for example, in yeast or plant cells. The recombinant protein may be present at the C-terminus or N-terminus of the fusion protein, and optionally contain a protease restriction site that enables the foreign protein to be cleaved from the forisome body following purification. The isolation and purification of the obtained artificial forisomes is performed by cell disruption and e.g., centrifugation/density gradient centrifugation. Alternatively, the protein polymer can be converted from the solid state polymer to a soluble state, in particular following mutation of one or more of the above-described C-terminal conserved cysteines by means of high Ca$^{2+}$ concentration (<2 mM), or by a combination of high Ca$^{2+}$ concentration (<2 mM) and reducing conditions (>18.5 µm NaHSO$_3$). Thus, forisome technology presents an entirely new purification system that completely omits traditional methods such as precipitation, filtration, and chromatography, and instead is based on centrifugation and the conformational state of the protein. Based on this technology, purification of a variety of proteins can be simplified and the cost reduced. In addition, the purification system offers the advantage that toxic effects or interactions of the proteins to be purified with the membrane can be minimized or prevented by fusion to forisomes. Using this approach, the malaria antigen MSP1$_{19}$ for example was successfully purified by the present invention; this is extremely difficult by other means due to the strong interaction of MSP1$_{19}$ with the membrane. The purification is illustrated by immunological detection of the antigen, which is shown in FIG. 7.

3) Purification of Antibodies

The invention enables purification of polyclonal or monoclonal antibodies to be performed using artificial forisomes, thereby avoiding previous chromatographic separation steps. For this purpose, the antigen is cloned upstream or downstream to a forisome gene (MtSEO-F1 or MtSEO-F2 or MtSEO-F4 and/or a portion thereof, as defined above) by the methods described previously. The antigen-MtSEO-F-fusion product is subsequently expressed in yeast, optionally together with MtSEO-F1 and MtSEO-F4 having C-terminal and/or N-terminal deletions of up to 13 amino acids. This procedure yields artificial forisomes that contain the antigen in the yeast cells.

The yeast cells are grown, pelleted by centrifugation, and the cells disrupted. The artificial forisomes carrying the antigen are now free in solution and can be used to purify the polyclonal or monoclonal antibodies as follows.

The antigen-containing artificial forisomes are incubated with antibody serum, whereby the specific antibodies bind to the artificial forisomes. The forisome are pelleted by centrifugation, washed, and the antibodies subsequently eluted via a pH change. The antibody solution is then neutralized and can now be used for various applications (Western blot, immunoprecipitation, ELISA, antibody therapy, etc.).

4) Modification of Forisomes Properties

With the help of the invention, forisomes can be modified artificially to acquire new, technologically useful properties. For example, the binding of forisomes to surfaces can be improved by including SEO-F subunits fused to protein or (protein or peptide) tags in said forisomes. This approach enables their positioning and immobilization in microchannels. Examples include the fusion with the B-domain of the *Staphylococcus aureus* protein A, with glutathione S-transferase or with biotin, which allows selective surface functionalization of the artificial forisome produced in the organism and subsequent isolation in a manner that enables their covalent binding to surfaces coated with IgG, glutathione, or streptavidin. As before, stable forisome can be obtained when a SEO-F subunit capable of forming homomers in the absence of other subunits is coexpressed with the fusion protein, or the foreign protein component in the expression product is not too large. This circumvents problems associated with accurate positioning of forisomes employed as mechanoproteins to surfaces or to micro channels. If a fusion is performed with a further SEO-F protein instead of with a foreign protein, a mechanoprotein body is obtained having conformational change properties that can be modified by the $Ca^{2+}$ concentration and pH.

The following examples of specific embodiments are intended to deepen the understanding of the invention.

EXAMPLE 1

Enzyme Immobilization Using Artificial Forisomes (Enzyme Coupling)

I. The forisome genes MtSEO-F1 and MtSEO-F2 and MtSEO-F4 with and without translational stop codon were amplified from *M. truncatula* cDNA using the following oligonucleotides (the restriction sites are underlined):

```
MtSEO-F1 fw NcoI:
5'-AGA ACC ATG GGA TCA TTG TCC AAT GGA

ACT AAA C-3'

MtSEO-F1 rev XhoI with stop:
5'-AGA CTC GAG TCA TAT CTT GCC ATT CTG

TGG AGC-3'

MtSEO-F1 rev XhoI without stop:
5'-AGA CTC GAG CAT ATC TTG CCA TTC TGT

GGA GC-3'

MtSEO-F2 fw NcoI:
5'-AGA ACC ATG GGA TCC ACT GCA TTG TCC

TAT AAT G-3'

MtSEO-F2 rev XhoI with stop:
5'-AGA CTC GAG TCA AAT GCA ACT ATC TGG-3'

MtSEO-F2 rev XhoI without stop:
5'-AGA CTC GAG ATG CAG CAA CTA TCT GGA-3'

MtSEO-F4 fw NcoI:
5'-AGA ACC ATG GGA TCC CTT TCC AAC TTA

GGA AG-3'

MtSEO-F4 rev XhoI with stop:
5'-AGA CTC GAG TCA AAC ACC AAG ATT GTT

TGG-3'

MtSEO-F4 rev XhoI without stop:
5'-AGA CTC GAG ACA CCA AGA TTG TTT GGT

TC-3'
```

The amplicons were digested with the restriction enzymes NcoI/XhoI and cloned into the corresponding restriction sites of the pENTR4™ vector (Invitrogen, Germany). In this way, pENTR4-MtSEO-F vectors with and without stop codons were generated.

II. The genes of the enzymes hexokinase 2 (HXK2), phosphoglucoisomerase (PGI) and glucose-6-phosphate dehydrogenase (G6PDH) from *Saccharomyces cerevisiae* were amplified as cDNA using the following oligonucleotides (the restriction sites are underlined).

```
G6PDH fw XhoI:
5'-AGA CTC GAG AAT GAG TGA AGG CCC CGT C-3'

G6PDH rev XhoI:
5'-AGA CTC GAG CTA ATT ATC CTT CGT ATC TTC-3'

HXK2 fw XhoI:
5'-AGA CTC GAG AAT GGT TCA TTT AGG TCC AAA-3'

HXK2 rev XhoI:
5'-AG ACT CGA GTT AAG CAC CGA TGA TAC CA-3'

PGI XhoI fw:
5'-AGA CTC GAG AAT GTC CAA TAA CTC ATT CAC-3'

PGI XhoI rev:
5'-AGA CTC GAG ATC ACA TCC ATT CCT TGA ATT

G-3'

Invertase XhoI fw:
5'-AGA CTC GAG AGC ATC AAT GAC AAA CGA AAC-3'

Invertase XhoI rev:
5'-AGA CTC GAG CTA TTT TAC TTC CCT TAC TTG

G-3'
```

The amplicons were digested with XhoI and cloned into the corresponding restriction site of the pENTR4-MtSEO-F vectors without stop (see a) I). In this way, the following vectors were obtained: pENTR4-MtSEO-F1-G6PDH, pENTR4-MtSEO-F2-G6PDH, pENTR4-MtSEO-F4-G6PDH, pENTR4-MtSEO-F1-HXK2, pENTR4-MtSEO-F2-HXK2, pENTR4-MtSEO-F4-HXK2, pENTR4-MtSEO-F1-PGI, pENTR4-MtSEO-F2-PGI and pENTR4-MtSEO-F4-PGI.

III. The vectors pENTR4-MtSEO-F1 with stop and pENTR4-MtSEO-F4 with stop were recombined with the yeast vectors 425GPD-ccdB (Addgene, USA). The resulting expression constructs 425GPD-MtSEO-F1 and 425GPD-MtSEO-F4 were transformed into the yeast strain InvSc1 (Invitrogen, Germany). For selection, the correction of the yeast strain leucine auxotrophy was used. The resulting yeast cells produce artificial forisomes of MtSEO-F1 or MtSEO-F4 that were used as the basis for enzyme coupling.

IV. The above-mentioned pENTR4 vectors with MtSEO-F-enzyme fusions (see 1.II.) were recombined with the yeast vector 424GPD-ccdB (Addgene, USA). The resulting vectors (424GPD-MtSEO-F1-G6PDH, 424GPD-MtSEO-F2-G6PDH, 424GPD-MtSEO-F4-G6PDH, 424GPD-MtSEO-F1-HXK2, 424GPD-MtSEO-F2-HXK2, 424GPD-MtSEO-F4-HXK2, 424GPD-MtSEO-F1-PGI, 424GPD-MtSEO-F2-PGI, 424GPD-MtSEO-F4-PGI) were each transformed into yeast that already contained a plasmid (425GPD-MtSEO-F1 or 425GPD-MtSEO-F4) to generate artificial forisomes of MtSEO-F1 or MtSEO-F4 (see a) III.) The resulting double mutants (e.g., 425GPD-MtSEO-F1/424GPD-MtSEO-F2-G6PDH) are therefore corrected for their leucine as well as tryptophan auxotrophy.

V. Expression yeasts producing enzyme-coupled forisomes (see a) I.-IV.) were grown in a volume of 50 ml until the $OD_{600nm}$ was between 5-7 and harvested by centrifugation (1000×g, 10 min). The yeast pellet was washed with 50 ml of V-medium (10 mM Tris, 10 mM EDTA, 100 mM KCl, pH 7.4), centrifuged again (1000×g, 10 min) and frozen at −20° C. The frozen cell pellet was resuspended in 1 ml V-medium, and approximately 500 mg glass beads (425-600 μm) were added. The cells were disrupted in 1.5 ml tubes at 30 Hz in the Mixer Mill MM400 (Retsch, Germany). The artificial forisome with the insoluble cell components were subsequently pelleted by centrifugation and resuspended in 0.5 ml V-medium. The solution was loaded on a sucrose or Nycodenz density gradient in which the sucrose or Nycodenz concentration increased from 40% to 70%. The gradient was centrifuged in a Beckman ultracentrifuge at 163,000×g at 4° C. for 3 h.

The forisome-containing phase was subsequently removed from the gradient with a pipette, diluted 1:2 with V-medium and divided into 2 equal aliquots. The aliquots were centrifuged for 10 minutes at 100×g and the supernatant removed. The forisomes of the first aliquot were then taken up in 50 μl V-medium and used to determine the molecular mass and concentration of the enzyme-coupled artificial forisomes by SDS-polyacrylamide gel electrophoresis (SDS-PAGE). The second aliquot was taken up in 50 μl enzyme buffer (for G6PDH-coupled forisomes: 250 mM glycylglycine buffer, pH 7.4; HXK2-coupled forisomes: 0.05 M Tris-HCl buffer with 13.3 mM $MgCl_2$, pH 8; PGI-coupled forisomes: 250 mM glycylglycine buffer, pH 7.4). This aliquot was used to determine the activity of the forisomen-coupled enzymes using specific enzyme assays.

VI. The molecular mass and concentration of enzyme-coupled, artificial forisomes (see a) IV) were determined by SDS-PAGE analysis. The different forisome proteins comprising the enzyme-linked, artificial forisomes (e.g., MtSEO-F1 and MtSEO-F2 enzyme fusion protein) are thereby separated. The presence of the individual proteins was determined by comparing the mass predicted by bioinformatics (e.g., MtSEO-F2-G6PDH=124.7 kilodaltons) with the actual mass of the protein in the gel (MtSEO-F2-G6PDH=approx. 130 kDa). The protein concentration was determined using a standard series of defined protein amounts that was loaded simultaneously and/or by using the protein marker Precision Plus Protein Standards unstained (Bio-Rad). We were able to obtain a total amount of protein (single MtSEO-F protein+MtSEO-F-enzyme fusion) between 56-124 μg of artificial, enzyme-linked forisomes, depending on the selected forisome protein and enzyme fusion, from a 50 ml yeast expression culture. The proportion of MtSEO-F-enzyme fusion relative to the total protein content is between 10%-50% depending on the fusion partner. We obtained the largest quantities, both of total protein (124 μg/50 ml culture) and enzyme fusion protein (37 μg/50 ml culture) when PGI-coupled enzyme forisomes were generated (MtSEO-F1/MtSEO-F2-PGI).

The activity of the forisome-immobilized enzymes was determined by specific spectrophotometric enzyme assays. For glucose-6-phosphate dehydrogenase, the protocol recommended by Sigma-Aldrich (Germany) was used. The assay is based on the G6PDH-catalyzed conversion of glucose-6-phosphate into 6-phosphogluconolactone. In this reaction, nicotinamide adenine dinucleotide phosphate ($NADP^+$) is reduced to NADPH:

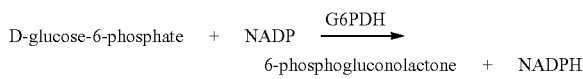

Figure 6:
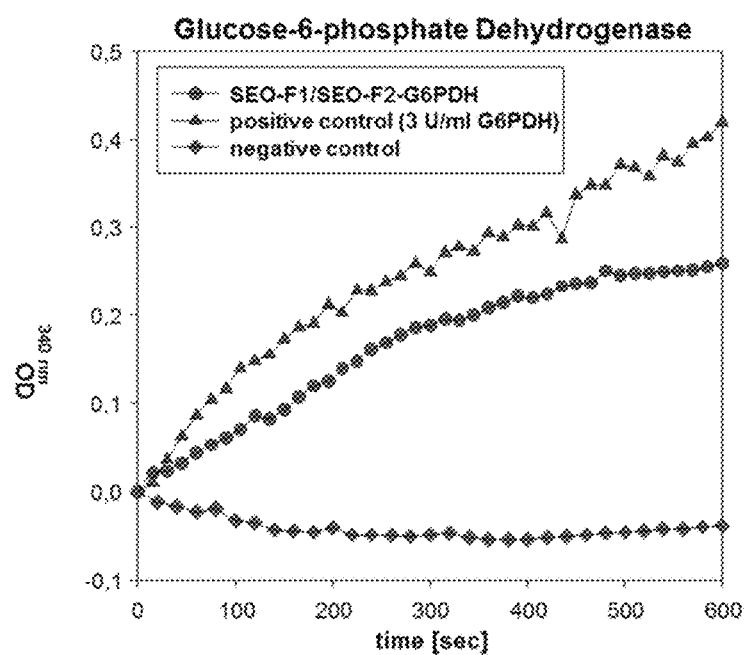
FIG. 6 shows an enzyme activity assay of glucose-6-phosphate dehydrogenase that is coupled to the forisome bodies SEO-F1 and SEO-F2 of the invention.

The absorbance of NADPH in the wavelength range of 340 nm can be measured photometrically and used to calculate enzyme activity. For this assay, the purified enzyme forisomes from the second aliquot (see a) V.) were used. Using the determined concentration of the enzyme-linked forisomes (see a) VI.) the measured enzyme activities per gram of artificial forisome was calculated. Depending on the construct (see a) III.) activities between 2000-2700 Units per gram of artificial forisome were obtained for forisome-immobilized glucose-6-phosphate dehydrogenase. In comparison, glucose-6-phosphate dehydrogenase immobilized to agarose beads that is commercially available from Sigma-Aldrich (Germany) has only between 1000 to 1750 Units per gram of agarose. Thus, the forisome-immobilized glucose-6-phosphate dehydrogenase of the present invention exhibits a markedly higher specific enzyme activity (enzyme activity based on the amount of carrier material). FIG. 6 shows an enzyme activity assay of glucose-6-phosphate dehydrogenase that is coupled to the forisome bodies SEO-F1 and SEO-F2 of the invention.

The activity of forisome-immobilized hexokinase 2 and phosphoglucoisomerase was determined using a similar assay principle. In this case, only two successive enzyme reactions were used to measure the enzyme activity based on the increase of NADPH absorbance at 340 nm. For hexokinase 2, the protocol recommended by Worthington (Lakewood, N.J., USA) was used, which is based on the following reaction:

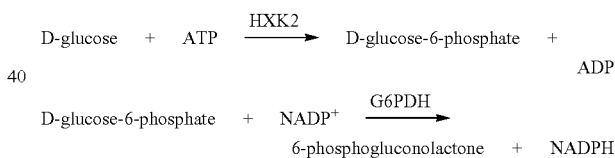

Glucose-6-phosphate dehydrogenase required for the second reaction was added to the assay in the form of commercially available soluble enzyme with a defined activity. Depending on the construct (see a) III.) activities between 6000-8000 Units per gram of artificial forisome were obtained for forisome-immobilized hexokinase 2. In contrast, agarose-immobilized hexokinase available from Sigma-Aldrich has an activity of only 50-75 U.

For phosphoglucoisomerase, the protocol recommended by Sigma-Aldrich (Germany) was used which is based on the following reaction:

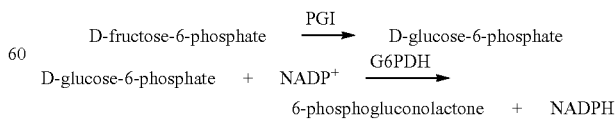

Depending on the construct (see a) III.), activities between 6000-8000 Units per gram of artificial forisome were obtained for forisome-immobilized phosphoglucoisomerase. In contrast, agarose-immobilized phosphoglucoisomerase available from Sigma-Aldrich has an activity of only 300-600 U.

EXAMPLE 2

Purification of Proteins 2.1 Purification of Recombinant Proteins Using Unmutated Forisome Genes or in Absence of Unmutated Forisome Genes I. The coding sequence of a fragment of the malaria surface antigen MSP (MSP$_{19}$) was amplified from a sequence within a vector using the following oligonucleotides (restriction sites are underlined).

```
MSP19 NcoI fw:
5'-AGACCATGGACCTGCGTATTTCTCAG-3'

MSP19 NcoI FaXa rev:
5'-AGACCATGGTACGACCTTCGATCCTGCATATAGAAATGCC-3'

MSP19 XhoI FaXa fw:
5'-AGACTCGAGAATCGAAGGTCGTGACCTGCGTATTTCTCAG-3'

MSP19 XbaI rev:
5'-AGATCTAGATCACCTGCATATAGAAATG-3'
```

The primers MSP$_{19}$ NcoI FaXa rev and MSP$_{19}$ XhoI FaXa fw contain the coding sequence of the recognition site for the protease Factor Xa (shown in italics) in addition to the gene-specific sequences. The first amplicon was treated with the restriction enzyme NcoI and cloned into the NcoI site of the vectors pENTR4-MtSEO-F1 with stop codon, pENTR4-MtSEO-F2 with stop codon and pENTR4-MtSEO-F4 with stop codon (see a) I.) to generate the vectors pENTR4-MSP$_{19}$-MtSEO-F1, pENTR4-MSP$_{19}$-MtSEO-F2 and pENTR4-MSP$_{19}$-MtSEO-F4. The second amplicon was treated with the restriction enzymes XhoI and XbaI, and cloned into the XhoI/XbaI-restriction sites of the vectors pENTR4-MtSEO-F1 without stop codon, pENTR4-MtSEO-F2 without stop codon and pENTR4-MtSEO-F4 without stop codon (see a) I.) to generate the vectors pENTR4-MtSEO-F1-MSP$_{19}$, pENTR4-MtSEO-F2-MSP$_{19}$ and pENTR4-MtSEO-F4-MSP$_{19}$. For preparation of the expression vectors 424GPD-MSP$_{19}$-MtSEO-F1, 424GPD-MSP$_{19}$-MtSEO-F2, 424GPD-MSP$_{19}$-MtSEO-F4, 424GPD-MtSEO-F1-MSP$_{19}$, 424GPD-MtSEO-F2-MSP$_{19}$ and 424GPD-MtSEO-F4-MSP$_{19}$ the generated vectors were recombined with the yeast vector 424GPD-ccdB (Addgene, USA).

II. The vectors 424GPD-MSP$_{19}$-MtSEO-F4 and 424GPD-MtSEO-F4-MSP$_{19}$ were transformed into the yeast strain InvSc1 (Invitrogen, Germany) using the correction of tryptophan auxotrophy of the yeast strain for selection. The fusion proteins comprised of MSP$_{19}$ and MtSEO-F4 form forisomes without additional expression of an additional MtSEO-F protein.

The vectors 424GPD-MSP$_{19}$-MtSEO-F1, 424GPD-MSP$_{19}$-MtSEO-F2, 424GPD-MtSEO-F1-MSP$_{19}$ and 424GPD-MtSEO-F2-MSP$_{19}$ were transformed into yeast that already contained a plasmid (425GPD-MtSEO-F1) to generate artificial forisomes of MtSEO-F (see a) III.). The resulting yeast (e.g., 425GPD-MtSEO-F1/424GPD-MSP$_{19}$-MtSEO-F1) are corrected for their leucine and tryptophane auxotrophy and provide artificial forisomes fused to the MSP$_{19}$ protein.

III. The artificial forisomes fused to MSP$_{19}$ were purified as described in 1.V and detected and quantified by SDS-PAGE and Western blotting. All constructs were suitable for purification. However, the inventors obtained the highest purification yield of 0.42 mg MSP$_{19}$ protein per liter of cell culture with the 424GPD-MPS$_{19}$-Mt.SEO-F4 construct. Future optimization by modifying culture and purification conditions will lead to higher yields of protein available for purification. Furthermore, the MSP$_{19}$ protein can be cleaved from the artificial protein by incubation with Factor Xa protease. In addition, the inventors have observed that certain reducing and calcium-containing buffer conditions (4 mM $CaCl_2$, 200 μm $NaHSO_3$, 10 mM TRIS, 100 mM KCl, pH 7.2) can lead to disassembly of artificial forisomes (especially when the cysteines in position 615 and 620 of the MtSEO-F1 protein are mutated). This conversion from the insoluble form to the soluble form may also be used for protein isolation and purification. FIG. 7 shows the purification of MSP$_{19}$ using forisome bodies of SEO-F1 or SEO-F4. The immunological detection of MPS1$_{19}$ is shown.

2.1b Purification of Recombinant Proteins Using Forisome Genes Containing Mutated Cysteines The cysteines located at positions 3 and 8 in the sequence motif (FIG. 5) of the MtSEO-F1gene were mutated to serines using the QuikChange II Site-Directed Mutagenesis Kit from Agilent Technologies (CA, USA) according to manufacturers instructions. The vector pENTR4-MtSEO-F1 with and without stop codons (Example 1) served as a substrate. The cysteines at position 3 and position 8 correspond to amino acids 615 and 620 of the MtSEO-F1 protein. The resulting mutated MtSEO-F1 gene is therefore hereinafter named MtSEO-F1 (C615S/C620S).

The coding sequence of a fragment of the malaria surface antigen MSP (MSP$_{19}$) was cloned into the vector pENTR4™ (Invitrogen, Germany) upstream and downstream of MtSEO-F1 (C615S/C620S) as described in Example 2.1a.

By recombination of the vector pENTR4-MtSEO-F1 (C615S/C620S) with the yeast vectors 425GPD-ccdB (Addgene, USA) and recombination of the vectors pENTR4-MSP$_{19}$-MtSEO-F1 (C615S/C620S) and pENTR4-MtSEO-F1(C615S/C620S)-MSP$_{19}$ with the yeast vectors 424GPD-ccdB (Addgene, USA), the expression vectors 425GPD-MtSEO-F1(C615S/C620S), 424GPD-MSP$_{19}$-MtSEO-F1 (C615S/C620S), 424GPD-MtSEO-F1 (C615S/C620S)-MSP$_{19}$ [were generated].

The following combinations of yeast vectors were transformed into the yeast strain InvSc1 (Invitrogen, Germany) 425GPD-MtSEO-F1(C615S/C620S)+424GPD-MSP$_{19}$-MtSEO-F1(C615S/C620S)
and
425GPD-MtSEO-F1(C615S/C620S)+424GPD-MtSEO-F1 (C615S/C620S)-MSP$_{19}$ The correction of the leucine and tryptophan auxotrophy of the yeast strain was used for selection. The resulting yeasts produce artificial forisomes comprised of MtSEO-F1 (C615S/C620S) that contain MSP$_{19}$ protein.

Almost 100% of the resulting artificial forisomes can be converted into the soluble form with reducing buffer containing calcium ions (4 mM $CaCl_2$, 200 μm $NaHSO_3$, 10 mM TRIS, 100 mM KCl, pH 7.2), while only a small proportion of the non-mutated version converts to the soluble form.

The purification process can thereby be abbreviated. After cultivation, the yeast cells containing artificial forisomes with MSP$_{19}$ protein can be disrupted, the artificial forisome and yeast components separated from soluble components by centrifugation, and the protein-forisome-fusions products then brought into solution.

2.2 Purification of Antibodies Using Artificial Forisomes

I. The coding sequence of the Small Rubber Particle Protein 3 (SRPP3) was amplified from sequences within a vector with the following oligonucleotides (restriction sites are underlined).

```
SRPP3 XhoI fw:
5'-AGA CTCGAG A ATGACCGACGCTGCTTC-3'

SRPP 3 XhoI rev:
5'-AGA CTCGAG TCATGTTTCCTCCACAATC-3'
```

The amplicon was treated with the restriction enzyme XhoI and cloned into the XhoI site of the vector pENTR4-MtSEO-F1 without stop codon (see a) I.) to generate the vector pENTR4-MtSEO-F1-SRPP3. To generate the expression vector 424GPD-MtSEO-F1-SRPP3 the resulting vector was recombined with the yeast vector 424GPD-ccdB (Addgene, USA).

II. The vector 424GPD-MtSEO-F1-SRPP3 was transformed into yeast cells that already contained a plasmid (425GPD-MtSEO-F1) to produce artificial forisomes of MtSEO-F1 (see 1.III.). The resulting yeasts (e.g., 425GPD-MtSEO-F1/424GPD-MtSEO-F1-SRPP3) are corrected for their leucine and tryptophan auxotrophy and present artificial forisomes fused to the SRPP3 protein. The yeasts were grown in a volume of 50 ml to $OD_{600}$, centrifuged and resuspended in 1 ml V-medium (10 mM Tris, 10 mM EDTA, 100 mM KCl, pH 7.4), and disrupted by means of a ball mill. The artificial forisomes carrying the antigen were then free in solution and could be used in the following for purification of polyclonal or monoclonal antibodies.

Figure 8:
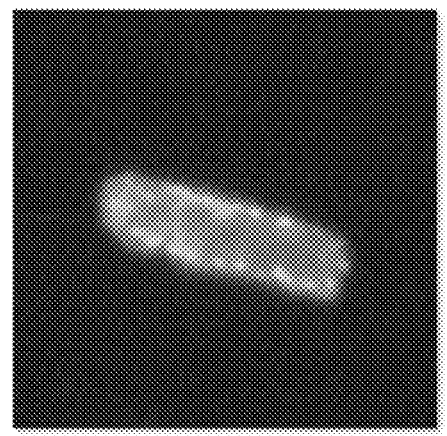
FIG. 8 shows the use of the interaction between the B-domain and the IgG antibody for immobilization of artificial forisomes.

III. The artificial forisomes containing antigen were incubated for 30 minutes with 500 µl of a polyclonal anti-SRPP3 serum that was produced in rabbit. The specific antibodies thereby bound to the artificial forisomes. The forisomes were pelleted by centrifugation (4000×g, 4 min), and washed three times with 1 ml PBS (137 mM NaCl, 2.7 mM KCl, 10 mM $Na_2HPO_4$, 2 mM $KH_2PO_4$, pH 7.4). Then the antibodies were eluted with 450 µl 0.1 M glycine-HCl solution (pH 2.7) for 5 min. Subsequently, the antibody solution was neutralized with 50 µl 1 M Tris-HCl solution (pH 8.5). Subsequent blots demonstrated the high specificity of the purified antibody was detectable (without serum contamination). The antibodies purified by means of the forisome technology were used for various purposes (Western Blot, immunoprecipitation, ELISA, antibody therapy, etc.). The principle of this purification is shown in FIG. 7; FIG. 8 shows the use of the interaction between the B-domain and the IgG antibody for immobilization of artificial forisomes. An artificial forisome consisting of SEO-F1 subunits coupled to the B-domain binds fluorescent IgG antibodies.

EXAMPLE 3

Immobilization of Artificial Forisomes to Technical Surfaces (Surface Coupling)

I. The coding sequence of glutathione-S-transferase (GST) was amplified from sequences within the pGex-3X vector (GE Healthcare, USA) using the following oligonucleotides (restriction sites are underlined).

```
GST NcoI XhoI fw:
5'-AGA CCA TGG GAC TCG AGA ATG TCC CCT

ATA CTA GGT TA-3'

GST SalI rev:
5'-AGA GTC GAC TTA ACG ACC TTC GAT CAG

ATC-3'
```

The fragment was treated with the restriction enzymes NcoI/SalI and cloned into the NcoI/XhoI-digested pENTR4™ cloning vector, resulting in the vector pENTR4-GST. Subsequently, the amplicon containing the MtSEO-F1 gene with stop (see FIG. 1.1.) was cloned into the NcoI/XhoI-sites of the resulting vector to generate the vector pENTR4-GST-MtSEO-F1. To generate the expression vector 424GPD-GST-MtSEO-F1, the vector pENTR4-GST-MtSEO-F1 was recombined with the yeast vector 424GPD-ccdB (Addgene, USA). The expression vector was transformed into yeasts cells that already contained a plasmid (425GPD-MtSEO-F1) to produce artificial forisomes of MtSEO-F1 (see a) III.). The resulting yeast (425GPD-MtSEO-F1/424GPD-GST-MtSEO-F1) are corrected for their leucine and tryptophan auxotrophy and present artificial forisomes with a GST-tag. They were purified as described in a) V. and the presence of the respective proteins (MtSEO-F1 and GST-MtSEO-F1) was detectable by SDS-PAGE. It was further shown that the resulting artificial GST-coupled forisomes bound to a glutathione-coupled matrix (Glutathione Sepharose 4B, Amersham Bioscience, USA).

II. The coding sequence of the B domain of *Staphylococcus aureus* protein A was amplified from sequences within the vector 424GPD-ccdB-TAP (Addgene, USA) using the following oligonucleotides (restriction sites are underlined).

```
B domain NcoI fw:
5'-AGACCATGGCGGATAACAAATTCAACA-3'

B domain NcoI rev:
5'-AGACCATGGCTTTTGGTGCTTGAGCATC-3'

B domain XhoI fw:
5'-AGACTCGAGAGCGGATAACAAATTCAAC-3'

B domain XhoI rev:
5'-AGACTCGAGTCATTTTGGTGCTTGAGCATC-3'
```

The first amplicon was treated with the restriction enzyme NcoI and cloned into the NcoI restriction site of pENTR4-MtSEO-F1 with stop codon and pENTR4-MtSEO-F4 with stop codon (see a) I) to generate the vectors pENTR4-B-domain-MtSEO-F1 and pENTR4-B-domain-MtSEO-F4. The second amplicon was treated with the restriction enzyme XhoI and cloned into the XhoI restriction site of the vector pENTR4-MtSEO-F1 without stop codon and pENTR4-MtSEO-F4 without stop codon (see a) I.) to generate the vectors pENTR4-MtSEO-F1-B-domain and pENTR4-MtSEO-F4-B-domain. To produce the expression vectors 424GPD-B-domain-MtSEO-F1, 424GPD-B-domain-MtSEO-F4, 424GPD-MtSEO-F1-B-domain, 424GPD-MtSEO-F4-B domain, the vectors produced were recombined with the yeast vector 424GPD-ccdB (Addgene, USA).

The vectors 424GPD-B-domain-MtSEO-F4 and 424GPD-MtSEO-F4-B-domain were transformed into the yeast strain InvSc1 (Invitrogen, Germany). For selection, the correction of tryptophan auxotrophy of the yeast strain was used. The fusion proteins of the B domain and MtSEO-F4 assembled to forisome-like structures without additional expression of another MtSEO-F protein.

The vectors 424GPD-B-domain-MtSEO-F1 and 424GPD-MtSEO-F1-B-domain were transformed into yeast that already contained a plasmid (425GPD-MtSEO-F1) to produce artificial forisomes of MtSEO-F1 (see 1.III.). The resulting yeasts (e.g., 425GPD-MtSEO-F1/424GPD-B-domain-MtSEO-F1) are corrected for their leucine and tryptoph anauxotrophy and present artificial forisomes fused to a B-domain. All of the artificial forisomes generated that contained B-domains bound to IgG-coupled Sepharose (GE Healthcare, USA).

2.3 Preparation and Purification of Artificial SEO-F Forisomes Containing Two Different SEO-F Proteins 2.3.1: Fusion of Amino Acids 1-96 of MtSEO-F4 and Amino Acids 73-648 of MtSEO-F1.

The N-terminal MtSEO-F4-fragment and the C-terminal MtSEO-F1 fragment were amplified with the oligonucleotides

```
MtSEO-F4 MSLSN NcoI fw
5'-AGACCATGGGATCCCTTTCCAACTTAGGAAGTG -3'

MtSEO-F4 LISCQ NcoI rev
5'-AGACCATGGCCTGACAAGAAATCAGCTT-3'

MtSEO-F1 MITTR NcoI fw
5'-AGACCATGGGAATGATAACCACCCCTC-3'

MtSEO-F1 QNGKI XhoI rev
5'-AGACTCGAGGTCATATCTTGCCATTCTGTGGAG-3'
``` and cloned into the NcoI/XhoI-digestion pENTR4 vector. The resulting vector pENTR4-MtSEO-F4(1-288 bp)/MtSEO-F1(219-1944 bp) was subsequently recombined with the plant expression vector pBatTL and the yeast expression vector 425GPD-ccdB. The resulting pBatTL-MtSEO-F4(1-288 bp)/MtSEO-F1(219-1944 bp) was transformed into *Agrobacterium*, which was used to infiltrate *N. benthamiana* plants (see Müller et al., 2010). The resulting vector 425GPD-MtSEO-F4(1-288 bp)/MtSEO-F1(219-1944 bp) was transformed into the yeast strain InvSc1. In both systems, the development of artificial forisomes was observed microscopically. The purification was carried out as described above in Example 1 V.

2.3.2: Fusion of Amino Acids 1-583 of MtSEO-F1 with Amino Acids 620-670 of MtSEO-F2.

The N-terminal MtSEO-F1 fragment and the C-terminal MtSEO-F2 fragment were amplified using the oligonucleotides

```
MtSEO-F1 MSLNS NcoI fw
5'-AGACCATGGGATCATTGTCCAATGGAACTA-3'

MtSEO-F1 FKEYY XhoI rev
5'-AGACTCGAGTGATAGTATTCTTTGAATGCAAT-3'

MtSEO-F2 DTKLS XhoI fw
5'-AGACTCGAGTGATACTAAGCTTTCAGAGAT-3'

MtSEO-F2 DSCCI XhoI 5'-rev
AAACTCGAGTCAAATGCAGCAACTATCTGGATCATC-3'
``` and cloned into the NcoI/XhoI-digested vector pENTR4. The resulting vector pENTR4-MtSEO-F1(1-1749 bp)/MtSEO-F2(1860-2010 bp) was recombined with the plant expression vector pBatTL and the yeast expression vector 425GPD-ccdB. The generated pBatTL-MtSEO-F1(1-1749 bp)/MtSEO-F2 (1860-2010 bp) was transformed into *Agrobacterium*, which was used to infiltrate *N. benthamiana* plants (see Müller et al., 2010). The resulting vector 425GPD-MtSEO-F1(1-1749 bp)/MtSEO-F2(1860-2010 bp) was transformed into the yeast strain InvSc1. In both systems, the formation of artificial forisome could be observed microscopically. The purification was carried out as described in Example 1 V above.

SEQUENCE LISTING

```
<160> NUMBER OF SEQ ID NOS: 47

<210> SEQ ID NO 1
<211> LENGTH: 647
<212> TYPE: PRT
<213> ORGANISM: Medicago truncatula
<220> FEATURE:
<221> NAME/KEY: SOURCE
<222> LOCATION: 1..647
<223> OTHER INFORMATION: /mol_type="protein"
      /note="MtSEO-F1"
      /organism="Medicago truncatula"

<400> SEQUENCE: 1

Met Ser Leu Ser Asn Gly Thr Lys Leu Pro Asn Pro Phe Asp Leu Asp
1               5                   10                  15

Glu Ser Gln Ile Leu Asp Lys Val Tyr Leu Thr His Leu His Asp Asp
            20                  25                  30

Asp Lys Cys Asp Lys Asp Val Leu Phe His Ile Leu Ser Asn Val Ile
        35                  40                  45

Leu Arg Thr Arg Leu Ala Glu Ser Arg Ala Glu Phe Glu Pro Glu Phe
    50                  55                  60

Arg Thr Leu Lys Leu Ile Ser Cys Gln Met Ile Thr Thr Pro Arg Gly
65                  70                  75                  80

Glu Arg Tyr Val His Gln Thr Thr Met Trp Ile Leu Gln Gln Leu Lys
```

```
            85                  90                  95
Thr Tyr Ser Trp Asp Ala Lys Ala Leu Ile Ala Leu Ala Ala Phe Thr
            100                 105                 110
Leu Glu Tyr Gly Asn Leu Leu Tyr Leu Thr Glu Thr Ser Thr Ser Ser
            115                 120                 125
Asp Gln Leu Val Asn Ser Leu Lys Ile Leu Asn Gln Ile Gln Asn Arg
            130                 135                 140
Lys Val Thr Val Pro Ala Thr Asp Leu Val Glu Leu Ile Met Asp Val
145                 150                 155                 160
Leu Leu His Ile His Glu Trp Ala Thr Arg Ser Gly Val Gly Tyr Asn
                165                 170                 175
Thr Leu Asp Val Pro Ser Leu Ser Asp Ala Leu Gln Asp Ile Pro Val
            180                 185                 190
Ala Val Tyr Trp Ile Ile Ala Ser Thr Val Ala Ala Thr Gly Asn Ile
            195                 200                 205
Ile Gly Val Ser Asp Tyr Thr Leu Ser Asp Phe Lys Glu Lys Leu Asn
            210                 215                 220
Phe Val Asp Ser Lys Leu Lys Glu His Leu Lys Leu Ser Lys Trp Gln
225                 230                 235                 240
Ile Asp Ser Val Glu Glu Tyr Leu Lys Arg Lys Lys Ala Ile Ser Asn
                245                 250                 255
Pro Lys Asp Ile Ile Asp Phe Leu Lys Leu Leu Ile Gln Arg Asn Gly
            260                 265                 270
Asp Asn Leu Leu Ile Tyr Asp Gly Thr Thr Lys Asn Lys Thr Asp Ile
            275                 280                 285
Glu Val Phe Lys Asp Lys Tyr Val Leu Leu Phe Ile Ser Ser Leu Asn
            290                 295                 300
Lys Val Asp Asp Glu Ile Leu Leu Leu Asn Ser Ile His Asp Arg Leu
305                 310                 315                 320
Gln Asp Asn Pro Gln Val Ile Lys Gly Tyr Lys Lys Glu Asp Phe Lys
                325                 330                 335
Ile Leu Trp Ile Pro Ile Trp Asp Val Asp Asp Gln Lys Ile Lys Phe
            340                 345                 350
Asp Ser Leu Lys Asn Lys Ile Arg Phe Tyr Ala Val Asp Tyr Phe Ser
            355                 360                 365
Glu Leu Pro Gly Ile Arg Leu Ile Arg Glu His Leu Asn Tyr Ser Asp
            370                 375                 380
Lys Pro Ile Val Pro Val Leu Ser Pro Leu Gly Glu Lys Met Asn Asp
385                 390                 395                 400
Asp Ala Met Asp Leu Ile Phe Gln Trp Gly Ile Asp Ala Leu Pro Phe
                405                 410                 415
Arg Lys Gln Asp Gly Tyr Asp Leu Thr Gln Lys Trp Lys Trp Phe Trp
            420                 425                 430
Asp Val Thr Lys Arg Val Asn Leu Gly Ile Gln Val Lys Gly Asp Arg
            435                 440                 445
Tyr Ile Phe Ile Tyr Gly Gly Ser Asp Lys Lys Trp Ile Gln Asp Phe
            450                 455                 460
Thr Leu Ala Leu Glu Lys Thr Lys Arg His Glu Thr Ile Leu Arg Ala
465                 470                 475                 480
Asp Ala Ile Ile Glu His Tyr His Leu Gly Lys Asp Asp Pro Lys Ile
                485                 490                 495
Val Pro Arg Phe Trp Ile Glu Ile Glu Ser Lys Arg Leu Lys Lys His
            500                 505                 510
```

```
Gln Asp Gly Ile Asp Cys Glu Ile Gln Asp Ile Val Lys Ser Leu Leu
            515                 520                 525

Cys Leu Lys Gln Asp Pro Gln Gly Trp Val Ile Leu Thr Lys Gly Tyr
        530                 535                 540

Asn Val Lys Leu Leu Gly His Gly Glu Pro Met Tyr Gln Thr Leu Ala
545                 550                 555                 560

Asp Phe Asp Ile Trp Lys Asp Arg Val Leu Gln Lys Glu Gly Phe Asp
                565                 570                 575

Ile Ala Phe Lys Glu Tyr Tyr Asp Thr Lys Val Lys Asp Thr Tyr Val
            580                 585                 590

Lys Gln Pro Cys Glu Ile Ile Asn Val Asp Asn Ile Asn Gly Asn
        595                 600                 605

Val Ile Ala Thr Ile Ser Cys Pro Asn Pro Thr Cys Gly Arg Val Met
        610                 615                 620

Glu Val Ser Ser Val Asn Tyr Lys Cys Cys His Arg Asp Asp Ala Ala
625                 630                 635                 640

Ala Pro Gln Asn Gly Lys Ile
                645

<210> SEQ ID NO 2
<211> LENGTH: 675
<212> TYPE: PRT
<213> ORGANISM: Medicago truncatula
<220> FEATURE:
<221> NAME/KEY: SOURCE
<222> LOCATION: 1..675
<223> OTHER INFORMATION: /mol_type="protein"
      /note="MtSEO-F2"
      /organism="Medicago truncatula"

<400> SEQUENCE: 2

Met Ser Thr Ala Leu Ser Tyr Asn Val Pro Ile Ser Gly Thr Thr Thr
1               5                   10                  15

Gln Lys Asn Asp Thr Ser Gln Gln Lys Ser Gln Leu Pro Asn Pro
            20                  25                  30

Phe Lys Leu Glu Asp Ile Glu Ile Leu Asn Lys Val Tyr Leu Thr His
        35                  40                  45

Val Asn Asp Asn Met Lys Tyr Asp Arg Asp Thr Leu Phe Asn Leu Val
50                  55                  60

Ser Asn Ile Ile Ser Ala Ser Thr Gln Thr Ser Gly Thr Asn Ser Gly
65                  70                  75                  80

Leu Asn Thr Gln Ile Ser Phe Lys Pro Asp Phe Ser Val Leu Lys Arg
                85                  90                  95

Ile Ser Cys Gln Met Ile Thr Thr Arg Gly Thr Ala Glu Cys Ala His
            100                 105                 110

Gln Thr Thr Met Trp Val Leu His His Leu Arg Gly Phe Ser Trp Glu
        115                 120                 125

Ala Lys Ala Leu Ile Thr Leu Ala Ala Phe Ser Leu Glu Tyr Gly Ala
    130                 135                 140

Ile Met His Leu His Arg Ile Gln Ser Ser Asp Thr Leu Gly Asn Ser
145                 150                 155                 160

Leu Lys Gln Leu Ser Gln Val Gln Phe Arg Lys Val Pro Ala Asp Ile
                165                 170                 175

Thr Glu Leu Val Thr Phe Leu Leu Gln Val Leu Gln Asp Ile Lys Thr
            180                 185                 190

Trp Ala Ala Trp Ser Ala Phe Gly Tyr Asp Leu Asp Asp Val Asn Ser
```

-continued

```
            195                 200                 205
Leu Pro Asp Ala Met Gln Trp Ile Pro Leu Val Val Tyr Trp Thr Val
210                 215                 220

Ala Thr Ile Val Ala Cys Thr Gly Asn Leu Val Gly Ile Ser Glu His
225                 230                 235                 240

Lys Leu Ser Asp Tyr Val Lys Ser Leu Ser Asp Val Val Lys Glu Leu
                245                 250                 255

Arg Arg His Leu Lys Ser Cys Glu Leu Glu Ile Gly Lys Ile His Glu
                260                 265                 270

Asn Glu Asn Leu Leu Lys Asp Ser Asp Asn Ile Lys Asp Val Val Ala
                275                 280                 285

Phe Leu Arg Leu Leu Ile Lys Gly Asn Gly Thr Asp Gln Ile Pro Pro
290                 295                 300

Ile Phe Ile Gly Asn Asp Gln Val Lys Thr Gly Ile Glu Val Phe Lys
305                 310                 315                 320

Lys Lys His Val Leu Leu Phe Val Ser Gly Leu Asp Thr Leu Arg Asp
                325                 330                 335

Glu Ile Leu Leu Leu Asn Ser Ile Tyr Lys Arg Leu Gln Asp Lys Pro
                340                 345                 350

Gln Glu Val Leu Lys Gly Ser Phe Lys Lys Glu Asp Phe Lys Ile Leu
                355                 360                 365

Trp Ile Pro Ile Val Asn Lys Trp Asp Glu Asp Arg Lys Lys Glu Phe
370                 375                 380

Lys Asn Leu Lys Glu Ser Met Lys Trp Tyr Val Leu Glu His Phe Ser
385                 390                 395                 400

Glu Leu Pro Gly Arg Gly Ile Ile Lys Lys Lys Leu Asn Tyr Asp Ile
                405                 410                 415

Gly Tyr Pro Pro Ile Leu Ala Val Ile Asn Pro Gln Gly Asp Ile Ile
                420                 425                 430

Asn Lys Asp Ala Met Glu Ile Ile Phe Gln Trp Gly Ile Asp Ala Phe
                435                 440                 445

Pro Phe Arg Ile Ser Asp Ala Glu Asp Ile Phe Lys Lys Trp Glu Trp
450                 455                 460

Phe Trp Lys Leu Met Lys Lys Val Asp Val Asn Ile Glu Lys Met Ser
465                 470                 475                 480

Trp Asp Arg Tyr Ile Phe Ile Tyr Gly Gly Asn Asp Pro Lys Trp Ile
                485                 490                 495

Gln Asp Phe Thr Arg Ala Ile Gly Ser Ile Lys Lys His Gln Thr Ile
                500                 505                 510

Gln Asn Val Asp Val Asn Ile Asp Tyr His Gln Leu Gly Lys Asn Asn
                515                 520                 525

Pro Thr Glu Ile Pro Tyr Phe Trp Met Gly Ile Asp Gly Arg Lys Gln
530                 535                 540

Gln Asn Lys Thr Cys Lys Asp Ser Val Asp Cys Glu Ile Gln Thr Ala
545                 550                 555                 560

Val Lys Lys Leu Leu Cys Leu Lys Gln Asp Pro Leu Gly Trp Val Leu
                565                 570                 575

Leu Ser Arg Gly Arg His Val Thr Val Phe Gly His Gly Glu Pro Met
                580                 585                 590

Tyr Gln Thr Val Ala Asp Phe Asp Lys Trp Lys Asn Asn Val Val Glu
                595                 600                 605

Lys Glu Ser Phe Asp Glu Ala Phe Lys Glu Tyr Tyr Asp Thr Lys Leu
                610                 615                 620
```

```
Ser Glu Ile Ser Ser Ala Ser Cys Ala Val Asn Ser Ser Asp Val
625                 630                 635                 640

Leu Ala Thr Ile Thr Cys Pro Asn Pro Phe Cys Gly Arg Val Met Glu
                645                 650                 655

Val Thr Ser Val Asn Tyr Lys Cys Cys His Arg Asp Asp Pro Asp Ser
            660                 665                 670

Cys Cys Ile
        675

<210> SEQ ID NO 3
<211> LENGTH: 701
<212> TYPE: PRT
<213> ORGANISM: Medicago truncatula
<220> FEATURE:
<221> NAME/KEY: SOURCE
<222> LOCATION: 1..701
<223> OTHER INFORMATION: /mol_type="protein"
      /note="MtSEO-F3"
      /organism="Medicago truncatula"

<400> SEQUENCE: 3

Met Ser Ser Ser Met Ala Pro Ser Ser Leu Val Ser Asn Val Ser Ala
1               5                   10                  15

Tyr Ser Gln Gln Ala Arg Thr Ser Asn Pro Leu Ala Trp Ser Asp Asp
                20                  25                  30

Lys Ile Leu Glu Thr Val Tyr Leu Thr His Val His Thr Gly Glu Arg
            35                  40                  45

Tyr Asp Val Glu Ser Leu Phe Asn Leu Thr Ser Asn Ile Leu Lys Arg
50                  55                  60

Ser Thr Ala Val Ala Asp Ser Val Ala Ser Lys Thr Gly Thr Pro Val
65                  70                  75                  80

Gly Leu Val Glu Asp Arg Leu Pro Leu Ser Gly Tyr Glu Pro Pro Ile
                85                  90                  95

Arg Lys Leu Lys His Ile Ser Ala Gln Met Met Ser Thr Leu Pro Gly
            100                 105                 110

Glu His His Ala His Met Thr Thr Met Ser Ile Leu Asp Gln Leu Lys
        115                 120                 125

Ser His Thr Trp Asp Gly Lys Ala Ile Phe Ala Leu Ala Ala Phe Ser
    130                 135                 140

Leu Glu Tyr Gly Asn Phe Trp His Leu Val Gln Thr Pro Ser Gly Asp
145                 150                 155                 160

Thr Leu Gly Arg Ser Leu Ala Thr Met Asn Arg Val Gln Ser Val Asp
                165                 170                 175

Lys Asn Arg Gln Ala Ile Ala Asp Tyr Asn Ser Leu Val Lys Asn Leu
            180                 185                 190

Leu Phe Ala Val Glu Cys Ile Thr Glu Leu Glu Lys Leu Ser Thr Lys
        195                 200                 205

Gly Tyr Glu His Lys Asp Val Pro Ala Leu Ser Glu Ala Met Gln Glu
    210                 215                 220

Ile Pro Val Ala Val Tyr Trp Ala Ile Ile Thr Ala Ile Ile Cys Ala
225                 230                 235                 240

Asn His Leu Asp Leu Leu Phe Gly Asp Ser Asp Asp Arg Tyr Glu Leu
                245                 250                 255

Ser Ser Tyr Asp Val Lys Leu Ala Ser Ile Val Ser Lys Leu Lys Ala
            260                 265                 270

His Leu Thr Arg Ser Arg Lys His Ile Gly Glu Leu Glu Asp Tyr Trp
```

```
            275                 280                 285
Arg Arg Lys Arg Val Leu Gln Thr Pro Thr Glu Ile Val Glu Val Leu
290                 295                 300

Lys Val Leu Val Phe His Asn Glu Ile Gln Asp Pro Leu Val Phe Asp
305                 310                 315                 320

Gly Leu Asn Arg Gln Met Val Ser Ile Glu Val Phe Arg Lys Lys His
                    325                 330                 335

Val Leu Val Phe Ile Ser Gly Leu Asp Ser Ile Arg Asp Glu Ile Arg
                340                 345                 350

Leu Leu Gln Ser Ile Tyr Val Gly Leu Gln Glu Glu Pro Arg Glu Leu
            355                 360                 365

Lys Gly Tyr Arg Lys Glu Asp Phe Lys Ile Leu Trp Ile Pro Ile Val
370                 375                 380

Asp Asp Trp Thr Leu Leu His Lys Ala Glu Phe Asp Asn Leu Lys Leu
385                 390                 395                 400

Glu Met Pro Trp Tyr Val Val Glu Tyr Phe Tyr Pro Leu Ala Gly Ile
                    405                 410                 415

Arg Leu Ile Arg Glu Asp Leu Ser Tyr Lys Asn Lys Pro Ile Leu Pro
                420                 425                 430

Val Leu Asn Pro Leu Gly Arg Ile Val Asn His Asn Ala Met His Met
            435                 440                 445

Ile Phe Val Trp Gly Ile Asp Ala Phe Pro Phe Arg Pro Thr Asp Asp
450                 455                 460

Glu Ser Leu Thr Gln Lys Trp Asn Trp Phe Trp Ala Glu Met Lys Lys
465                 470                 475                 480

Val Tyr Pro Arg Leu Gln Asp Leu Ile Lys Gly Asp Thr Phe Ile Phe
                    485                 490                 495

Ile Tyr Gly Gly Thr Asp Pro Lys Trp Thr Gln Asp Phe Ala Leu Ala
                500                 505                 510

Ile Glu Lys Ile Lys Arg His Glu Ile Thr Arg Lys Ala Asp Ala Val
            515                 520                 525

Ile Glu His Phe His Phe Gly Lys Glu Asp Lys Arg Ile Val Pro Arg
            530                 535                 540

Phe Trp Ile Gly Ile Glu Ser Leu Phe Ala Asn Met Ile Gln Lys Lys
545                 550                 555                 560

His Lys Asp Pro Thr Ile Asp Glu Ile Lys Ser Leu Leu Cys Leu Lys
                    565                 570                 575

Gln Asp Gln Pro Gly Trp Val Leu Leu Ser Lys Gly Pro Asn Val Lys
                580                 585                 590

Leu Leu Gly Arg Gly Asp Gln Met Tyr Ala Thr Ala Val Asp Phe Glu
            595                 600                 605

Ile Trp Lys Glu Lys Val Leu Glu Lys Ala Gly Phe Asp Val Ala Phe
610                 615                 620

Lys Glu Tyr Tyr Glu Arg Lys Arg Arg Glu Tyr Pro Val Ala Cys Ala
625                 630                 635                 640

Asn Met Gln Leu Ala Asn Tyr Pro Ser Asp Ile Leu Asp Pro Ile Tyr
                    645                 650                 655

Cys Pro Asp Ser Asn Cys Gly Arg Ser Met Glu Ile Ala Ser Val Ser
                660                 665                 670

Tyr Lys Cys Cys His Gly His Thr His Glu Asn Ala Glu Val Ala Pro
            675                 680                 685

Ala Glu Ser Gly Gly Phe Val Gln Ile Glu Lys Arg Ser
690                 695                 700
```

<210> SEQ ID NO 4
<211> LENGTH: 671
<212> TYPE: PRT
<213> ORGANISM: Medicago truncatula
<220> FEATURE:
<221> NAME/KEY: SOURCE
<222> LOCATION: 1..671
<223> OTHER INFORMATION: /mol_type="protein"
      /note="MtSEO-F4"
      /organism="Medicago truncatula"

<400> SEQUENCE: 4

```
Met Ser Leu Ser Asn Leu Gly Ser Ala Thr Ala Thr Asn Ser Ser Leu
1               5                   10                  15

Asn Gln Lys Asn Ala Thr Asn Ser Leu Gln Asn Lys Ala Asn Phe Leu
            20                  25                  30

Pro Asn Pro Phe Asp Leu His Asp Pro Gln Ile Leu Asp Arg Val Tyr
        35                  40                  45

Leu Thr His Val Thr Asp Asp Glu Phe Cys Asp Thr Asn Ile Ile Phe
    50                  55                  60

Glu Leu Val Ser Ser Val Val Leu Gln Thr Ile Pro Lys Ile Ser Val
65                  70                  75                  80

Thr Ser Phe Lys Pro Glu Phe Pro Thr Leu Lys Leu Ile Ser Cys Gln
                85                  90                  95

Met Ile Thr Thr Arg Asn Asp Pro His Cys Val His Gln Thr Thr Leu
            100                 105                 110

Trp Ile Leu Gln Asn Leu Arg Ser Tyr Ser Trp Asp Ala Lys Ala Leu
        115                 120                 125

Ile Thr Leu Ala Ala Phe Thr Leu Glu Tyr Gly Asn Tyr Leu Gln Leu
    130                 135                 140

Asn Arg Val Thr Thr Thr Asp Thr Leu Gly Asn Ser Leu Arg Val Leu
145                 150                 155                 160

Asn Gln Val Gln Thr Arg Lys Ile Ser Asn Asp Val Thr Glu Leu Val
                165                 170                 175

Lys Tyr Ile Val Asp Met Leu Ile His Leu Asn Val Trp Ala Thr Trp
            180                 185                 190

Ser Ala Asp Gly Tyr Asp Pro Val Asp Val Pro Ala Leu Thr Asp Ala
        195                 200                 205

Leu Gln Glu Ile Pro Val Phe Val Tyr Trp Thr Ile Ala Ser Ile Val
    210                 215                 220

Ala Ser Thr Gly Asn Leu Val Gly Val Ser Asp Tyr Lys Leu Ser Ala
225                 230                 235                 240

Tyr Lys Glu Arg Leu Ser Arg Val Val Glu Glu Leu Val Lys His Leu
                245                 250                 255

Ala Thr Cys Glu Arg Gln Ile Arg Asn Val Asp Asp Leu Thr Ser Arg
            260                 265                 270

Thr Asn Asn Tyr Arg Lys Pro Lys Asp Ile Val Asp Cys Leu Lys Ala
        275                 280                 285

Leu Ile His Arg Asn Gly Thr Asp Ile Pro Gln Ile Tyr Gln Gly Asn
    290                 295                 300

Val Gln Val Lys Ser Gly Leu Asp Ile Phe Gln Lys His Val Leu
305                 310                 315                 320

Leu Phe Ile Ser Ser Leu Asp Arg Ile Gln Asp Glu Ile Thr Leu Leu
                325                 330                 335

Asn Ser Ile Tyr Glu Arg Leu Gln Glu Asn Pro Lys Glu Ser Lys Gly
```

```
                        340                 345                 350
        Phe Met Lys Glu Asp Phe Lys Ile Leu Trp Ile Pro Ile Val Lys Lys
                    355                 360                 365

Trp Asp Asp Ile Gln Ile Glu Asn Phe Lys Ala Leu Lys Ser Gly Ile
                370                 375                 380

Lys Trp Tyr Val Val Glu Tyr Phe Ser Glu Leu Pro Gly Leu Lys Ile
        385                 390                 395                 400

Ile Lys Asp Pro Glu Leu Ile Gly Tyr Ile Asp Asn Pro Ile Ile Pro
                        405                 410                 415

Val Phe Asn Pro Lys Gly Ile Ile Thr Asn Glu Asp Ala Met Asp Leu
                    420                 425                 430

Ile Phe Gln Trp Gly Ile Asp Ala Phe Pro Phe Arg Lys Ser Asp Gly
                435                 440                 445

Asn Asp Leu Lys Leu Lys Trp Asn Trp Leu Trp Asp Val Ile Lys Lys
                    450                 455                 460

Ala Thr Pro Gly Leu Leu Val Lys Val Asp Arg Tyr Ile Phe Ile Tyr
        465                 470                 475                 480

Gly Gly Thr Asn Lys Lys Trp Ile Gln Asp Phe Thr Leu Glu Leu Glu
                        485                 490                 495

Lys Ile Lys Arg His Glu Thr Ile Lys Arg Ala Asp Val Ile Ile Glu
                    500                 505                 510

Asn Tyr Gln Val Gly Lys Asp Pro Asn Arg Val Pro Ser Phe Trp
                515                 520                 525

Met Gly Ile Glu Arg Lys Lys Gln Asn Lys Lys His Gln Glu Thr Val
                    530                 535                 540

Asp Cys Lys Ile Gln Glu Ile Val Lys Asp Leu Phe Cys Leu Arg Arg
        545                 550                 555                 560

Asp Pro Gln Gly Trp Ile Ile Leu Ser Lys Gly His Ser Ile Lys Leu
                        565                 570                 575

Leu Gly His Gly Glu Pro Ala Tyr Gln Thr Leu Val Glu Phe Gln Asn
                    580                 585                 590

Trp Lys Asp Lys Val Leu Glu Lys Glu Gly Phe Asp Ile Ala Phe Lys
                595                 600                 605

Glu Tyr Tyr Gln Met Lys Ala Lys Glu Ile Ser Gly Arg Glu Pro Cys
        610                 615                 620

Glu Val Leu Asn Val Asp Thr Tyr Ser Ser Asn Val Ile Gly Thr Ile
        625                 630                 635                 640

Ser Cys Pro Asn Pro Met Cys Gly Arg Val Met Glu Val Ser Ser Ile
                        645                 650                 655

His Tyr Lys Cys Cys His Arg Asp Glu Pro Asn Asn Leu Gly Val
                    660                 665                 670

<210> SEQ ID NO 5
<211> LENGTH: 651
<212> TYPE: PRT
<213> ORGANISM: Dipteryx panamensis
<220> FEATURE:
<221> NAME/KEY: SOURCE
<222> LOCATION: 1..651
<223> OTHER INFORMATION: /mol_type="protein"
      /organism="Dipteryx panamensis"

<400> SEQUENCE: 5

Met Ser Leu Ser Asn Gly Ala Ser Ser Thr Thr Leu Ser Gln Gln Lys
1               5                   10                  15

Thr Gln Leu Pro Asn Pro Phe Asp Leu Thr Asp Ser Gln Ile Leu Asp
```

```
                    20                  25                  30
Lys Val Tyr Leu Ser His Ala His Asp Asp Glu Glu Cys Asp Arg Asp
            35                  40                  45

Thr Leu Leu Asp Leu Val Ser Ile Ile Ile Leu Lys Ser Gln Arg Pro
 50                  55                  60

Ile Pro Leu Ala Lys Tyr Lys Pro Glu Phe Pro Thr Leu Lys Leu Ile
 65                  70                  75                  80

Ser Cys Gln Met Ile Thr Thr Arg Gly Val Val His Cys Ala His Gln
                    85                  90                  95

Thr Thr Met Trp Ile Leu Gln His Leu Arg Ser Phe Ser Trp Asp Ala
            100                 105                 110

Lys Ala Leu Ile Thr Val Ala Ala Phe Ser Leu Glu Tyr Gly Asn Phe
            115                 120                 125

Arg His Leu Gln Ile Pro Thr Ser Asp Gln Leu Gly Asn Ala Leu Lys
            130                 135                 140

Gln Leu Asn Gln Val Asn Asn Gly Lys Leu Ser Asp Asp Ile Thr Glu
145                 150                 155                 160

Leu Ala Thr Val Thr Val Arg Val Leu Gln His Leu Lys Glu Trp Ala
                    165                 170                 175

Ala Trp Ser Ala Ala Gly Tyr Asp Thr Glu Asp Val Pro Ala Leu Ser
            180                 185                 190

Asp Ala Leu Gln Val Ile Pro Phe Val Val Tyr Trp Thr Ile Ala Ser
            195                 200                 205

Ile Val Ala Ser Thr Gly Asn Leu Ile Gly Val Ser Asp Tyr Lys Leu
            210                 215                 220

Ser Asp Phe Lys Asp Lys Leu Asp Arg Val Val Lys Thr Leu Asn Asp
225                 230                 235                 240

His Leu Asp Glu Cys Lys Lys Gln Ile Asp Val Ile Asp Asn Tyr Asn
                    245                 250                 255

Trp Arg Arg Lys Ala Phe Glu Asn Pro Lys Asp Ile Val Asp Leu Leu
            260                 265                 270

Lys Leu Leu Ile His Ser Lys Gly Ser Pro Ile Pro Gln Ile Tyr Asp
            275                 280                 285

Gly Arg Thr Thr Lys Thr Asp Ile Glu Val Phe Lys Gln Lys Tyr
            290                 295                 300

Val Leu Leu Phe Ile Ser Ser Leu Asp Ser Ile Asp Asp Glu Ile Arg
305                 310                 315                 320

Leu Leu Asn Ser Ile Tyr Asp Arg Leu Lys Glu Asp Pro Lys Glu Val
            325                 330                 335

Lys Gly Phe Asn Lys Glu Asp Phe Lys Ile Leu Trp Ile Pro Ile Val
            340                 345                 350

Asp Ser Trp Asp Lys Asp Ser Val Glu Lys Tyr Lys Thr Leu Lys Thr
            355                 360                 365

Lys Ile Lys Trp Tyr Ala Val Glu Phe Leu Ser Leu Val Pro Gly Ile
            370                 375                 380

Arg Leu Val Arg Glu Val Leu Lys Phe Glu Thr Lys Pro Ile Ile Pro
385                 390                 395                 400

Val Ile Ser Pro Gln Gly Lys Arg Ile Asn Asp Asn Ala Met Asp Ile
            405                 410                 415

Ile Phe Glu Trp Gly Val Asp Ala Phe Pro Phe Arg Lys Glu Asp Gly
            420                 425                 430

Asp Gln Leu Thr Gln Lys Trp Lys Trp Phe Trp Asp Val Ile Lys Lys
            435                 440                 445
```

```
Val Asn Pro Ala Ile Gln Val Glu Pro Glu Ser Tyr Ile Phe Ile Tyr
    450                 455                 460

Gly Gly Thr Asp Asn Lys Trp Ile Gln Asp Phe Thr Leu Ala Val Asp
465                 470                 475                 480

Lys Val Lys Arg His Asp Thr Ile Lys Arg Ala Asp Ala Ile Ile Glu
                485                 490                 495

His His Gln Leu Ala Lys Asp Asp Ser Ile Val Pro Arg Phe Trp Ile
                500                 505                 510

Gly Ile Glu Ser Lys Thr His Lys Lys His Gln Glu Ala Val Asp Cys
            515                 520                 525

Gln Ile Gln Thr Ile Val Lys Ser Leu Leu Cys Leu Lys Arg Asp Pro
530                 535                 540

Gln Gly Trp Ala Ile Leu Ser Lys Gly Asn Asn Val Lys Ile Leu Gly
545                 550                 555                 560

His Gly Glu Pro Met Leu Gln Thr Leu Thr Gln Phe Glu Ser Trp Lys
                565                 570                 575

Asp Lys Val Leu Glu Lys Glu Gly Phe Asp Ile Ala Leu Lys Glu Phe
                580                 585                 590

Tyr Asp Gly Lys Val Glu Ser Leu Ser Tyr Arg Gln Pro Cys Glu Tyr
            595                 600                 605

Leu Asn Ile Asp Ser Gln Ser Ser Ser Val Ile Ala Thr Ile Thr Cys
610                 615                 620

Pro Asn Pro Thr Cys Gly Arg Val Met Glu Val Thr Ser Val Asn Tyr
625                 630                 635                 640

Arg Cys Cys His Arg Asp Gly Gln Lys Ile Cys
                645                 650

<210> SEQ ID NO 6
<211> LENGTH: 668
<212> TYPE: PRT
<213> ORGANISM: Lotus japonicus
<220> FEATURE:
<221> NAME/KEY: SOURCE
<222> LOCATION: 1..668
<223> OTHER INFORMATION: /mol_type="protein"
      /organism="Lotus japonicus"

<400> SEQUENCE: 6

Met Ser His Val Pro Lys Ala Ala Ser Asn Gly Ala Leu Ile Gln His
1               5                   10                  15

Ser Gly Thr Ser Pro Asn Gln Lys Ala Tyr Leu Pro Ser Pro Phe Glu
                20                  25                  30

Leu Lys Asp Pro Gln Ile Leu Asp Arg Val Tyr Leu Thr His Val Asn
            35                  40                  45

Asp Asp Glu Ile Cys Asp Thr Lys Ile Leu Phe Asp Leu Val Ser Thr
    50                  55                  60

Val Val Leu Gln Ser Val Ser Gln Ile Pro Ala Thr Ser Phe Lys Pro
65                  70                  75                  80

Glu Phe Ser Thr Leu Lys Leu Ile Ser Cys Gln Met Ile Thr Thr Arg
                85                  90                  95

Asn Ala Asp His Cys Val His Gln Thr Thr Met Trp Ile Leu Gln Asn
                100                 105                 110

Leu Arg Ser Tyr Ser Trp Asp Ala Lys Ala Ile Ile Thr Leu Ala Ala
            115                 120                 125

Phe Thr Leu Glu Tyr Gly Asn Tyr Leu His Leu Ser Arg Ala Ala Val
    130                 135                 140
```

```
Ala Asp Thr Leu Gly Ser Ser Leu Arg Gln Leu Asn Gln Val His Thr
145                 150                 155                 160

Arg Lys Val Pro Ala Asp Ile Thr Lys Leu Val Thr Phe Ile Val His
                165                 170                 175

Ala Phe Gln His Leu Lys Glu Trp Ala Thr Trp Ala Asp Glu Gly Tyr
                180                 185                 190

Glu Pro Glu Glu Val Pro Ser Leu Thr Glu Ala Leu Gln His Val Pro
                195                 200                 205

Val Ala Val Tyr Trp Thr Ile Ala Ala Ile Val Ala Ser Thr Gly Asn
210                 215                 220

Leu Val Gly Val Ser Thr Tyr Asn Leu Gln Gly Tyr Ile Asp Arg Leu
225                 230                 235                 240

Asp Glu His Val Thr Lys Leu Ala Glu Gln Leu Asn Ser Cys Lys Leu
                245                 250                 255

Gln Ile Gly His Val Asp Asp Tyr Phe Asn Arg Arg Lys Ile Phe Asp
                260                 265                 270

Lys Pro Lys Asp Ile Val Asp Leu Leu Lys Ala Leu Ile His Arg Asn
                275                 280                 285

Gly Ala Gln Gly Pro Gln Ile Phe Glu Gly Gly Val Ile Val Lys Gln
290                 295                 300

Gly Leu Glu Val Phe Arg Gln Lys His Val Leu Leu Phe Ile Ser Gly
305                 310                 315                 320

Leu Asn Ser Ile Val Asp Glu Ile Leu Leu Leu Asn Ser Ile Tyr Asn
                325                 330                 335

Arg Leu Gln Asp Asn Pro Thr Glu Val Ile Lys Gly Phe Lys Lys Glu
                340                 345                 350

Asp Phe Lys Ile Leu Trp Val Pro Met Val Asp Arg Trp Asp Glu Ala
                355                 360                 365

Ser Arg Glu Gln Tyr Leu Asn Thr Trp Lys Arg Gly Ile Lys Trp Tyr
370                 375                 380

Ile Val Glu Tyr Phe Phe Glu Leu Pro Gly Arg Arg Ile Ile Thr Asp
385                 390                 395                 400

Pro Glu Arg Leu Gly Tyr Glu Gly Asn Pro Ile Pro Val Phe Asn
                405                 410                 415

Pro Gln Gly Met Leu Thr Asn Asp Asn Ala Met Asp Leu Ile Phe Gln
                420                 425                 430

Trp Gly Ile Asp Ala Phe Pro Phe Arg Lys Ser Asp Gly Ile Asp Leu
                435                 440                 445

Thr Leu Lys Trp Lys Trp Leu Trp Asp Ile Ile Lys Lys Ala Thr Pro
                450                 455                 460

Gly Leu Gln Val Lys Val Asp Arg Tyr Ile Phe Ile Phe Gly Ser Thr
465                 470                 475                 480

Asn Asn Lys Trp Ile Gln Asp Phe Thr Ile Glu Leu Asp Lys Leu Lys
                485                 490                 495

Arg Asn Glu Thr Val Lys Arg Ala Asp Val Ile Ile Glu Gln Tyr Gln
                500                 505                 510

Leu Gly Lys Asp Asp Pro Asn Arg Val Pro Ser Phe Trp Met Gly Val
                515                 520                 525

Glu Arg Lys Lys Gln Asn Lys Lys His Gln Glu Ala Val Asp Cys Glu
                530                 535                 540

Ile Gln Gly Ile Val Lys Ser Leu Phe Cys Leu Lys Arg Asp Pro Gln
545                 550                 555                 560
```

-continued

```
Gly Trp Val Ile Leu Ser Lys Gly His Asn Ile Lys Leu Leu Gly His
                565                 570                 575

Gly Glu Ala Val Tyr Gln Thr Val Val Glu Phe Pro Asn Trp Lys Glu
            580                 585                 590

Lys Val Leu Glu Arg Glu Gly Phe Asp Ile Ala Phe Lys Glu Tyr Tyr
        595                 600                 605

Asp Ile Lys Ala Lys Glu Ile Ser Ala Arg Gln Pro Cys Glu Ile Ile
610                 615                 620

Asn Val Asp Ser Tyr Ser Ala Asn Val Ile Ala Thr Ile Thr Cys Pro
625                 630                 635                 640

Asn Pro Met Cys Gly Arg Val Met Glu Val Thr Ser Val Asn Tyr Lys
                645                 650                 655

Cys Cys His Ser Asp Ala Pro Asn Gly Phe Gly Ile
                660                 665

<210> SEQ ID NO 7
<211> LENGTH: 685
<212> TYPE: PRT
<213> ORGANISM: Pisum sativum
<220> FEATURE:
<221> NAME/KEY: SOURCE
<222> LOCATION: 1..685
<223> OTHER INFORMATION: /mol_type="protein"
      /organism="Pisum sativum"

<400> SEQUENCE: 7

Met Ser Phe Ser Asn Ser Ala Ala Ala Thr Gly Thr Leu Val Gln
1               5                   10                  15

His Gly Gly Asn Ala Thr Asn Asn Ser Leu Ile Gln Lys Asn Ala
                20                  25                  30

Thr Ser Pro His Ser His His Lys Ala Asn Asn Tyr Leu Pro Asn Pro
            35                  40                  45

Phe Glu Leu His Asp Ser Gln Ile Leu Asp Lys Val Tyr Leu Thr His
        50                  55                  60

Val Thr Asp Asp Gln Phe Cys Asp Thr Asp Ile Ile Phe Asp Leu Val
65                  70                  75                  80

Ser Thr Leu Val Leu Gln Thr Asn Thr Gln Ile Pro Val Thr Gly Phe
                85                  90                  95

Lys Pro Asp Phe Pro Thr Leu Lys Leu Ile Ser Cys Gln Met Ile Thr
            100                 105                 110

Thr Arg Ser Ala Ala His Cys Val His Gln Thr Thr Leu Trp Ile Leu
        115                 120                 125

Gln Asn Leu Arg Ser Tyr Ser Trp Asp Ala Lys Ala Leu Ile Thr Leu
130                 135                 140

Ala Ala Phe Thr Leu Glu Tyr Gly Asn Tyr Leu His Leu Thr Arg Val
145                 150                 155                 160

Thr Ala Thr Asp Pro Ile Gly Asn Ser Leu Arg Gln Leu Asn Gln Ile
                165                 170                 175

Gln Thr Arg Asn Ile Ser Thr Asp Ile Thr Glu Leu Val Ser Phe Ile
            180                 185                 190

Val His Gln Leu Leu His Leu Lys Glu Trp Ala Thr Trp Ser Ala Glu
        195                 200                 205

Gly Tyr Asp Pro Glu Asp Val Pro Ala Leu Thr Glu Ala Leu Gln Glu
210                 215                 220

Ile Pro Val Phe Val Tyr Trp Thr Ile Ala Ser Ile Val Ala Ser Thr
225                 230                 235                 240
```

-continued

```
Gly Asn Leu Val Gly Val Ser Asp Tyr Lys Leu Ser Glu Tyr Arg Glu
            245                 250                 255

Arg Leu Ser Gly Ile Val Gln Lys Leu Val His Leu Asn Asn Cys
    260                 265                 270

Lys Leu Gln Ile Ser Tyr Ile Asp Asp Leu Phe Asn Arg Lys Lys Ile
        275                 280                 285

Phe Asp Lys Pro Lys Asp Ile Val Asp Cys Leu Lys Ala Leu Ile His
290                 295                 300

Arg Asn Gly Thr Asp Ser Pro Gln Ile Tyr Glu Gly Ala Ile His Val
305                 310                 315                 320

Lys Thr Gly Leu Glu Val Phe Arg Asn Lys His Val Leu Val Phe Ile
            325                 330                 335

Ser Ser Leu Asp Ser Ile Glu Asp Glu Ile Ser Leu Leu Asn Ser Ile
            340                 345                 350

Tyr Glu Arg Leu Gln Glu Asn Ser Lys Glu Ser Ile Lys Gly Phe Lys
        355                 360                 365

Lys Glu Asp Phe Lys Ile Leu Trp Ile Pro Ile Val Asn Asn Trp Asp
370                 375                 380

Asp Ile Arg Lys Glu Arg Phe Arg Ala Leu Lys Ser Gly Ile Lys Trp
385                 390                 395                 400

Tyr Ala Val Glu Tyr Phe Tyr Glu Leu Pro Gly His Arg Ile Ile Thr
            405                 410                 415

Asp Pro Glu Arg Ile Gly Tyr Ile Gly Asn Pro Ile Ile Pro Val Phe
        420                 425                 430

Asn Pro Gln Gly Tyr Ile Thr Asn Ile Asp Ala Met Asp Leu Ile Phe
        435                 440                 445

Gln Trp Gly Ile Asp Ala Phe Pro Phe Arg Lys Ser Asp Gly Ile Asp
    450                 455                 460

Leu Thr Leu Lys Trp Lys Trp Leu Trp Asp Val Ile Lys Lys Ala Thr
465                 470                 475                 480

Pro Gly Leu Gln Val Lys Gly Asp Arg Tyr Ile Phe Ile Tyr Gly Gly
            485                 490                 495

Thr Asn Asn Lys Trp Ile Gln Asp Phe Thr Leu Glu Leu Glu Lys Ile
        500                 505                 510

Lys Arg His Glu Ile Leu Lys Arg Ala Asp Val Ile Ile Glu Asn Tyr
    515                 520                 525

Gln Leu Gly Lys Glu Asp Pro Asn Arg Val Pro Ser Phe Trp Ile Gly
    530                 535                 540

Val Glu Arg Lys Lys Gln Asn Lys Lys His Gln Glu Ala Leu Asp Cys
545                 550                 555                 560

Glu Ile Gln Asp Ile Val Lys Ser Leu Phe Cys Leu Lys Arg Asp Pro
            565                 570                 575

Gln Gly Trp Ile Ile Leu Ser Lys Gly Gln Asn Ile Lys Leu Leu Gly
        580                 585                 590

His Gly Glu Pro Ala Tyr Gln Thr Leu Ala Glu Phe Gln Asn Trp Lys
    595                 600                 605

Asp Arg Val Leu Glu Lys Glu Gly Phe Asp Ile Ala Phe Lys Glu Tyr
610                 615                 620

Tyr Glu Met Lys Ala Lys Glu Leu Ser Gly Arg Gln Pro Cys Glu Val
625                 630                 635                 640

Val Asn Val Asp Thr Tyr Ser Ser Asn Val Ile Ala Thr Ile Ala Cys
            645                 650                 655

Pro Asn Pro Met Cys Gly Arg Val Met Glu Val Ser Ser Ala His Tyr
```

Lys Cys Cys His Arg Asp Glu Pro Asn Asn Phe Gly Val
        675                 680                 685

<210> SEQ ID NO 8
<211> LENGTH: 684
<212> TYPE: PRT
<213> ORGANISM: Vicia faba
<220> FEATURE:
<221> NAME/KEY: SOURCE
<222> LOCATION: 1..684
<223> OTHER INFORMATION: /mol_type="protein"
      /organism="Vicia faba"

<400> SEQUENCE: 8

Met Ser Phe Ser Asn Ser Pro Ala Ala Thr Gly Thr Leu Val Gln
1               5                   10                  15

His Gly Gly Asn Gly Thr Asn Ser Leu Ile Gln Lys Thr Ala Thr
                20                  25                  30

Ser Ser His Pro His His Lys Ala Asn Asn Tyr Leu Pro Asn Pro Phe
        35                  40                      45

Glu Leu His Asp Ser His Ile Leu Asp Lys Val Tyr Leu Thr His Val
50                  55                      60

Thr Asp Asp Glu Phe Cys Asp Thr Asp Ile Ile Phe Asp Leu Val Ser
65                  70                      75                  80

Thr Leu Ile Leu Gln Ser Asn Thr Gln Ile Pro Val Thr Gly Phe Lys
                85                  90                      95

Pro Asp Phe Pro Thr Leu Lys Leu Ile Ser Cys Gln Met Ile Thr Thr
                100                 105                 110

Arg Ser Val Ala His Cys Val His Gln Thr Thr Leu Trp Ile Leu Gln
                115                 120                 125

Asn Leu Arg Ser Tyr Ser Trp Asp Ala Lys Ala Leu Ile Thr Leu Ala
130                 135                     140

Ala Phe Thr Leu Glu Tyr Gly Asn Tyr Leu Gln Leu Asn Arg Val Thr
145                 150                 155                 160

Ala Thr Asp Pro Ile Gly Asn Ser Leu Arg Gln Leu Asn Gln Ile Gln
                165                 170                 175

Thr Arg Lys Ile Ser Thr Asp Ile Pro Glu Leu Val Asn Phe Ile Val
                180                 185                 190

His Lys Leu Leu His Leu Lys Glu Trp Ala Ala Trp Ser Ala Glu Gly
                195                 200                 205

Tyr Asp Pro Glu Asp Val Pro Ala Leu Thr Glu Ala Leu Gln Glu Ile
210                 215                 220

Pro Val Phe Val Tyr Trp Thr Ile Ala Ser Ile Val Ala Ser Thr Gly
225                 230                 235                 240

Asn Leu Val Gly Val Ser Asp Tyr Asn Leu Ser Glu Tyr Arg Glu Arg
                245                 250                 255

Leu Ser Gly Ile Val Gln Lys Leu Val Val His Leu Asn Asn Cys Lys
                260                 265                 270

Leu Gln Ile Ser Tyr Ile Asp Asp Leu Phe Asn Arg Arg Lys Ile Phe
                275                 280                 285

Asp Lys Pro Lys Asp Ile Val Asp Cys Leu Lys Ala Leu Ile His His
                290                 295                 300

Asn Gly Ala Asp Ser Pro Gln Ile Tyr Glu Gly Ala Ile His Val Lys
305                 310                 315                 320

Thr Gly Leu Glu Val Phe Arg His Lys His Val Leu Met Phe Ile Ser 325                 330                 335
Ser Leu Asp Ser Ile Glu Asp Glu Ile Ser Leu Leu Asn Ser Ile Tyr
            340                 345                 350

Glu Arg Leu Gln Glu Asn Ser Lys Glu Ser Ile Lys Gly Phe Lys Lys
            355                 360                 365

Glu Asp Phe Lys Ile Leu Trp Ile Pro Ile Val Asn Asn Trp Asp Asp
            370                 375                 380

Ile Arg Lys Glu Arg Phe Arg Ala Leu Lys Ser Gly Ile Lys Trp Tyr
385                 390                 395                 400

Ala Val Glu Tyr Phe Tyr Glu Leu Pro Gly His Arg Ile Ile Thr Asp
            405                 410                 415

Pro Glu Arg Ile Gly Tyr Ile Gly Asn Pro Ile Ile Pro Val Phe Asn
            420                 425                 430

Pro His Gly Tyr Ile Thr Asn Ile Asp Ala Met Asp Leu Ile Phe Gln
            435                 440                 445

Trp Gly Ile Asp Ala Phe Pro Phe Arg Lys Ser Asp Gly Ile Asp Leu
            450                 455                 460

Thr Phe Lys Trp Lys Trp Leu Trp Asp Val Ile Lys Lys Ala Thr Pro
465                 470                 475                 480

Gly Leu Gln Val Lys Gly Asp Arg Tyr Ile Phe Ile Tyr Gly Gly Thr
            485                 490                 495

Asn Asn Lys Trp Ile Gln Asp Phe Thr Leu Glu Leu Glu Lys Ile Lys
            500                 505                 510

Arg His Glu Thr Leu Lys Arg Ala Asp Val Ile Ile Asp Asn Tyr Gln
            515                 520                 525

Leu Gly Lys Asp Asp Pro Asn Arg Val Pro Ser Phe Trp Ile Gly Val
            530                 535                 540

Glu Arg Lys Lys Gln Asn Lys Lys His Gln Glu Ala Val Asp Cys Glu
545                 550                 555                 560

Ile Gln Asp Ile Val Lys Ser Leu Phe Cys Leu Lys Arg Asp Pro Gln
            565                 570                 575

Gly Trp Val Ile Leu Ser Lys Gly Gln Asn Ile Lys Leu Leu Gly His
            580                 585                 590

Gly Glu Pro Ala Tyr Gln Thr Leu Ala Glu Phe Gln Asn Trp Lys Asp
            595                 600                 605

Arg Val Leu Glu Lys Glu Gly Phe Asp Ile Ala Phe Lys Glu Tyr Tyr
            610                 615                 620

Glu Met Lys Ala Lys Glu Leu Ser Gly Arg Glu Pro Cys Glu Val Val
625                 630                 635                 640

Asn Val Asp Thr Tyr Ser Ser Asn Val Ile Ala Thr Ile Ala Cys Pro
            645                 650                 655

Asn Pro Met Cys Gly Arg Val Met Glu Val Ser Ser Val His Tyr Lys
            660                 665                 670

Cys Cys His Arg Asp Glu Pro Asn Asn Phe Gly Val
            675                 680

<210> SEQ ID NO 9
<211> LENGTH: 238
<212> TYPE: PRT
<213> ORGANISM: Aequorea victoria
<220> FEATURE:
<221> NAME/KEY: SOURCE
<222> LOCATION: 1..238
<223> OTHER INFORMATION: /mol_type="protein"
      /organism="Aequorea victoria"

<400> SEQUENCE: 9

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 10
<211> LENGTH: 239
<212> TYPE: PRT
<213> ORGANISM: Venus
<220> FEATURE:
<221> NAME/KEY: SOURCE
<222> LOCATION: 1..239
<223> OTHER INFORMATION: /mol_type="protein"
      /organism="Venus"

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu

```
                100                 105                 110
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 11
<211> LENGTH: 34
<212> TYPE: DNA
<213> ORGANISM: null
<220> FEATURE:
<221> NAME/KEY: source
<222> LOCATION: 1..34
<223> OTHER INFORMATION: /mol_type="DNA"
      /organism=null

<400> SEQUENCE: 11
agaaccatgg gatcattgtc caatggaact aaac                          34

<210> SEQ ID NO 12
<211> LENGTH: 33
<212> TYPE: DNA
<213> ORGANISM: null
<220> FEATURE:
<221> NAME/KEY: source
<222> LOCATION: 1..33
<223> OTHER INFORMATION: /mol_type="DNA"
      /organism=null

<400> SEQUENCE: 12
agactcgagt catatcttgc cattctgtgg agc                           33

<210> SEQ ID NO 13
<211> LENGTH: 32
<212> TYPE: DNA
<213> ORGANISM: null
<220> FEATURE:
<221> NAME/KEY: source
<222> LOCATION: 1..32
<223> OTHER INFORMATION: /mol_type="DNA"
      /organism=null

<400> SEQUENCE: 13
agactcgagc atatcttgcc attctgtgga gc                            32

<210> SEQ ID NO 14
<211> LENGTH: 34
<212> TYPE: DNA
<213> ORGANISM: null
<220> FEATURE:
<221> NAME/KEY: source
<222> LOCATION: 1..34
```

<223> OTHER INFORMATION: /mol_type="DNA"
     /organism=null

<400> SEQUENCE: 14
agaaccatgg gatccactgc attgtcctat aatg                                    34

<210> SEQ ID NO 15
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
     /organism=null

<400> SEQUENCE: 15
agactcgagt caaatgcagc aactatctgg                                         30

<210> SEQ ID NO 16
<211> LENGTH: 27
<212> TYPE: DNA
<213> ORGANISM: null
<220> FEATURE:
<221> NAME/KEY: source
<222> LOCATION: 1..27
<223> OTHER INFORMATION: /mol_type="DNA"
     /organism=null

<400> SEQUENCE: 16
agactcgaga tgcagcaact atctgga                                            27

<210> SEQ ID NO 17
<211> LENGTH: 32
<212> TYPE: DNA
<213> ORGANISM: null
<220> FEATURE:
<221> NAME/KEY: source
<222> LOCATION: 1..32
<223> OTHER INFORMATION: /mol_type="DNA"
     /organism=null

<400> SEQUENCE: 17
agaaccatgg gatcccttc caacttagga ag                                       32

<210> SEQ ID NO 18
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
     /organism=null

<400> SEQUENCE: 18
agactcgagt caaacaccaa gattgtttgg                                         30

<210> SEQ ID NO 19
<211> LENGTH: 29
<212> TYPE: DNA
<213> ORGANISM: null
<220> FEATURE:
<221> NAME/KEY: source
<222> LOCATION: 1..29
<223> OTHER INFORMATION: /mol_type="DNA"
     /organism=null

<400> SEQUENCE: 19
agactcgaga caccaagatt gtttggttc                                29

<210> SEQ ID NO 20
<211> LENGTH: 28
<212> TYPE: DNA
<213> ORGANISM: null
<220> FEATURE:
<221> NAME/KEY: source
<222> LOCATION: 1..28
<223> OTHER INFORMATION: /mol_type="DNA"
      /organism=null

<400> SEQUENCE: 20
agactcgaga atgagtgaag gccccgtc                                 28

<210> SEQ ID NO 21
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
      /organism=null

<400> SEQUENCE: 21
agactcgagc taattatcct tcgtatcttc                               30

<210> SEQ ID NO 22
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
      /organism=null

<400> SEQUENCE: 22
agactcgaga atggttcatt taggtccaaa                               30

<210> SEQ ID NO 23
<211> LENGTH: 28
<212> TYPE: DNA
<213> ORGANISM: null
<220> FEATURE:
<221> NAME/KEY: source
<222> LOCATION: 1..28
<223> OTHER INFORMATION: /mol_type="DNA"
      /organism=null

<400> SEQUENCE: 23
agactcgagt taagcaccga tgatacca                                 28

<210> SEQ ID NO 24
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
      /organism=null

<400> SEQUENCE: 24
agactcgaga atgtccaata actcattcac                               30

<210> SEQ ID NO 25
<211> LENGTH: 31
<212> TYPE: DNA
<213> ORGANISM: null
<220> FEATURE:
<221> NAME/KEY: source
<222> LOCATION: 1..31
<223> OTHER INFORMATION: /mol_type="DNA"
      /organism=null

<400> SEQUENCE: 25
agactcgaga tcacatccat tccttgaatt g                          31

<210> SEQ ID NO 26
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
      /organism=null

<400> SEQUENCE: 26
agactcgaga gcatcaatga caaacgaaac                            30

<210> SEQ ID NO 27
<211> LENGTH: 31
<212> TYPE: DNA
<213> ORGANISM: null
<220> FEATURE:
<221> NAME/KEY: source
<222> LOCATION: 1..31
<223> OTHER INFORMATION: /mol_type="DNA"
      /organism=null

<400> SEQUENCE: 27
agactcgagc tattttactt cccttacttg g                          31

<210> SEQ ID NO 28
<211> LENGTH: 26
<212> TYPE: DNA
<213> ORGANISM: null
<220> FEATURE:
<221> NAME/KEY: source
<222> LOCATION: 1..26
<223> OTHER INFORMATION: /mol_type="DNA"
      /organism=null

<400> SEQUENCE: 28
agaccatgga cctgcgtatt tctcag                                26

<210> SEQ ID NO 29
<211> LENGTH: 40
<212> TYPE: DNA
<213> ORGANISM: null
<220> FEATURE:
<221> NAME/KEY: source
<222> LOCATION: 1..40
<223> OTHER INFORMATION: /mol_type="DNA"
      /organism=null

<400> SEQUENCE: 29
agaccatggt acgaccttcg atcctgcata tagaaatgcc                 40

<210> SEQ ID NO 30
<211> LENGTH: 40
<212> TYPE: DNA
<213> ORGANISM: null

```
<220> FEATURE:
<221> NAME/KEY: source
<222> LOCATION: 1..40
<223> OTHER INFORMATION: /mol_type="DNA"
      /organism=null

<400> SEQUENCE: 30
agactcgaga atcgaaggtc gtgacctgcg tatttctcag                    40

<210> SEQ ID NO 31
<211> LENGTH: 28
<212> TYPE: DNA
<213> ORGANISM: null
<220> FEATURE:
<221> NAME/KEY: source
<222> LOCATION: 1..28
<223> OTHER INFORMATION: /mol_type="DNA"
      /organism=null

<400> SEQUENCE: 31
agatctagat cacctgcata tagaaatg                                 28

<210> SEQ ID NO 32
<211> LENGTH: 27
<212> TYPE: DNA
<213> ORGANISM: null
<220> FEATURE:
<221> NAME/KEY: source
<222> LOCATION: 1..27
<223> OTHER INFORMATION: /mol_type="DNA"
      /organism=null

<400> SEQUENCE: 32
agactcgaga atgaccgacg ctgcttc                                  27

<210> SEQ ID NO 33
<211> LENGTH: 28
<212> TYPE: DNA
<213> ORGANISM: null
<220> FEATURE:
<221> NAME/KEY: source
<222> LOCATION: 1..28
<223> OTHER INFORMATION: /mol_type="DNA"
      /organism=null

<400> SEQUENCE: 33
agactcgagt catgtttcct ccacaatc                                 28

<210> SEQ ID NO 34
<211> LENGTH: 38
<212> TYPE: DNA
<213> ORGANISM: null
<220> FEATURE:
<221> NAME/KEY: source
<222> LOCATION: 1..38
<223> OTHER INFORMATION: /mol_type="DNA"
      /organism=null

<400> SEQUENCE: 34
agaccatggg actcgagaat gtcccctata ctaggtta                      38

<210> SEQ ID NO 35
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
```

/organism=null

<400> SEQUENCE: 35
agagtcgact taacgacctt cgatcagatc                                30

<210> SEQ ID NO 36
<211> LENGTH: 27
<212> TYPE: DNA
<213> ORGANISM: null
<220> FEATURE:
<221> NAME/KEY: source
<222> LOCATION: 1..27
<223> OTHER INFORMATION: /mol_type="DNA"
      /organism=null

<400> SEQUENCE: 36
agaccatggc ggataacaaa ttcaaca                                   27

<210> SEQ ID NO 37
<211> LENGTH: 28
<212> TYPE: DNA
<213> ORGANISM: null
<220> FEATURE:
<221> NAME/KEY: source
<222> LOCATION: 1..28
<223> OTHER INFORMATION: /mol_type="DNA"
      /organism=null

<400> SEQUENCE: 37
agaccatggc ttttggtgct tgagcatc                                  28

<210> SEQ ID NO 38
<211> LENGTH: 28
<212> TYPE: DNA
<213> ORGANISM: null
<220> FEATURE:
<221> NAME/KEY: source
<222> LOCATION: 1..28
<223> OTHER INFORMATION: /mol_type="DNA"
      /organism=null

<400> SEQUENCE: 38
agactcgaga gcggataaca aattcaac                                  28

<210> SEQ ID NO 39
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
      /organism=null

<400> SEQUENCE: 39
agactcgagt cattttggtg cttgagcatc                                30

<210> SEQ ID NO 40
<211> LENGTH: 33
<212> TYPE: DNA
<213> ORGANISM: null
<220> FEATURE:
<221> NAME/KEY: source
<222> LOCATION: 1..33
<223> OTHER INFORMATION: /mol_type="DNA"
      /organism=null

<400> SEQUENCE: 40

```
agaccatggg atccctttcc aacttaggaa gtg                                    33
```

\<210\> SEQ ID NO 41
\<211\> LENGTH: 28
\<212\> TYPE: DNA
\<213\> ORGANISM: null
\<220\> FEATURE:
\<221\> NAME/KEY: source
\<222\> LOCATION: 1..28
\<223\> OTHER INFORMATION: /mol_type="DNA"
      /organism=null

\<400\> SEQUENCE: 41

```
agaccatggc ctgacaagaa atcagctt                                          28
```

\<210\> SEQ ID NO 42
\<211\> LENGTH: 27
\<212\> TYPE: DNA
\<213\> ORGANISM: null
\<220\> FEATURE:
\<221\> NAME/KEY: source
\<222\> LOCATION: 1..27
\<223\> OTHER INFORMATION: /mol_type="DNA"
      /organism=null

\<400\> SEQUENCE: 42

```
agaccatggg aatgataacc acccctc                                           27
```

\<210\> SEQ ID NO 43
\<211\> LENGTH: 33
\<212\> TYPE: DNA
\<213\> ORGANISM: null
\<220\> FEATURE:
\<221\> NAME/KEY: source
\<222\> LOCATION: 1..33
\<223\> OTHER INFORMATION: /mol_type="DNA"
      /organism=null

\<400\> SEQUENCE: 43

```
agactcgagg tcatatcttg ccattctgtg gag                                    33
```

\<210\> SEQ ID NO 44
\<211\> LENGTH: 30
\<212\> TYPE: DNA
\<213\> ORGANISM: null
\<220\> FEATURE:
\<221\> NAME/KEY: source
\<222\> LOCATION: 1..30
\<223\> OTHER INFORMATION: /mol_type="DNA"
      /organism=null

\<400\> SEQUENCE: 44

```
agaccatggg atcattgtcc aatggaacta                                        30
```

\<210\> SEQ ID NO 45
\<211\> LENGTH: 32
\<212\> TYPE: DNA
\<213\> ORGANISM: null
\<220\> FEATURE:
\<221\> NAME/KEY: source
\<222\> LOCATION: 1..32
\<223\> OTHER INFORMATION: /mol_type="DNA"
      /organism=null

\<400\> SEQUENCE: 45

```
agactcgagt gatagtattc tttgaatgca at                                     32
```

\<210\> SEQ ID NO 46

```
<211> LENGTH: 30
<212> TYPE: DNA
<213> ORGANISM: null
<220> FEATURE:
<221> NAME/KEY: source
<222> LOCATION: 1..30
<223> OTHER INFORMATION: /mol_type="DNA"
      /organism=null

<400> SEQUENCE: 46
agactcgagt gatactaagc tttcagagat                              30

<210> SEQ ID NO 47
<211> LENGTH: 36
<212> TYPE: DNA
<213> ORGANISM: null
<220> FEATURE:
<221> NAME/KEY: source
<222> LOCATION: 1..36
<223> OTHER INFORMATION: /mol_type="DNA"
      /organism=null

<400> SEQUENCE: 47
aaactcgagt caaatgcagc aactatctgg atcatc                       36
```

What is claimed is:

1. An artificial forisome body comprising a fusion protein of a SEO-F (Sieve Element Occlusion by Forisome) protein having the amino acid sequence of SEQ ID NO: 1, or a fragment of the amino acid sequence of SEQ ID NO: 1, wherein said fragment results from deleting up to 45 amino acids from the C-terminus and/or up to 13 amino acids from the N-terminus of the amino acid sequence of SEQ ID NO: 1, and at least one additional protein, wherein the at least one additional protein is not a fluorescent protein, and is selected from the group consisting of glucose-6-phosphate dehydrogenase, hexokinase, phospho-glucoisomerase and antibodies, and
wherein the forisome body further comprises an unfused SEO-F protein, wherein said unfused SEO-F protein is
(i) a protein having the amino acid sequence of SEQ ID NO: 1, or (ii) a protein comprising a fragment of the amino acid sequence of SEQ ID NO: 1, wherein said fragment results from deleting up to 45 amino acids from the C-terminus and/or up to 13 amino acids from the N-terminus of the amino acid sequence of SEQ ID NO: 1,
and wherein the unfused SEO-F protein has the ability to form homomeric forisome bodies in the absence of additional SEO-F proteins.

* * * * *